United States Patent [19]

Su et al.

[11] Patent Number: 5,939,428
[45] Date of Patent: Aug. 17, 1999

[54] ALKYL N-[3-(ACRIDIN-9-YL)AMINO-5-HYDROXYMETHYL] PHENYLCARBAMATES

[75] Inventors: Tsann-Long Su, Taipei, Taiwan; Ting-Chao Chou, Paramus, N.J.; Felicia Y.-H. Wu; Cheng-Wen Wu, both of Taipei, Taiwan

[73] Assignee: National Health Research Institutes, Taiwan

[21] Appl. No.: 09/073,025

[22] Filed: May 4, 1998

Related U.S. Application Data

[63] Continuation of application No. 08/667,257.
[51] Int. Cl.[6] .................................................... A61K 31/47
[52] U.S. Cl. .............................................. 514/297; 546/106
[58] Field of Search ............................... 546/106; 514/297

[56] References Cited

U.S. PATENT DOCUMENTS 5,354,864  10/1994  Watanabe et al. ........................ 546/106

OTHER PUBLICATIONS

Scarborough et al Chem. Abstr. vol. 125, Entry 265027, 1996.
Denney et al. Chem Abstr vol. 96 Entry 79437m, 1982.
Su et al., 1995, "9–Substituted Acridine Derivatives with Long Half–life and Potent Antitumor activity: Synthesis and Structure–Activity Relationships" J. Med. Chem. 38(17):3226–3235.
Su et al. 1996, "New acridine carbamate derivatives as potent topoisomerase II–mediated antitumor agents" Abstract #2004, Proc. Amer. Assoc. Cancer Res. 37 (Mar. 1996) p. 295.

*Primary Examiner*—Donald G. Daus
*Attorney, Agent, or Firm*—Banner & Witcoff, Ltd.

[57] ABSTRACT

The invention provides a compound of the following formula:

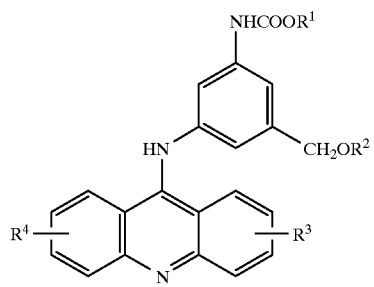

Formula (I)

wherein $R^1$ is $C_{1-6}$ alkyl; or phenyl;

$R^2$ is hydrogen;
  an acyl group of the formula —$COR^a$ wherein $R^a$ is $C_{1-6}$ alkyl or phenyl; or
  an acetylalkylcarbonyl group of the formula —$CO(CH_2)_nCOCH_3$ wherein $n=1–3$; and $R^3$ and $R^4$ are substituents at different position(s) of the acridine ring (i.e. C-1'–C-8'), and $R^3$ and $R^4$ may be the same or different and independently represent:
  hydrogen;
  $C_{1-6}$ alkyl;
  $C_{1-6}$ alkyloxy;
  a nitro group;
  an amino group of the formula —$NR^bR^c$ wherein $R^b$ and $R^c$ may be the same or different and independently represent hydrogen or $C_{1-6}$ alkyl;
  an aminoalkylamino group of the formula —$NH(CH_2)_nNR^dR^e$ wherein $R^d$ and $R^e$ may be the same or different and independently represent hydrogen, $C_{1-6}$ alkyl, a hydroxyalkyl group of the formula —$(CH_2)_nOH$ wherein $n=1–3$, or $C_{1-6}$ haloalkyl;
  an alkylaminocarbonyl group of the formula —$CONHR^f$ wherein $R^f$ is $C_{1-6}$ alkyl;
  an alkylaminoalkylaminocarbonyl group of the formula —$CONH(CH_2)_nNR^gR^h$ wherein $n=1$-$5$, and $R^g$ and $R^h$ may be the same or different and independently represent hydrogen, $C_{1-6}$ alkyl, or a nitro group;
  a halogen group;
  a hydroxyalkyl group of the formula —$CH_2)_nOH$ wherein $n=1–3$;
  a carbamate group of the formula —$CH_2CONHR^f$ wherein $R^f$ is as defined above;
  an alkylcarbonyloxymethyl group of the formula —$CH_2OCOR^f$ wherein $R^f$ is as defined above;
  alkyl sufonate of the formula —$SO_3R^f$ is as defined above; and
  an alkylsulfonyl group of the formula —$SO_2R^f$ wherein $R^f$ is as defined above;

with the proviso that when $R^2$, $R^3$ and $R^4$ are hydrogen, $R^1$ is not t-butyl;

and the pharmaceutically acceptable salts thereof.

The present invention also relates to a process for synthesizing the above-identified compound, intermediate compounds produced thereby, pharmaceutical compositions comprising the above compounds, and uses and method thereof for treating diseases.

6 Claims, No Drawings

ALKYL N-[3-(ACRIDIN-9-YL)AMINO-5-HYDROXYMETHYL]PHENYLCARBAMATES

This application is a continuation of application Ser. No. 08/667,257 now abandoned.

FIELD OF THE INVENTION

The invention relates to N-[3-(acridin-9-yl)amino-5-hydroxymethyl]phenylcarbamate derivatives, the processes and intermediates for their preparation, pharmaceutical compositions and uses of the derivatives and of the intermediates, and methods of treating diseases using them.

BACKGROUND OF THE INVENTION

9-Anilinoacridine derivatives have been extensively studied as potential antitumor agents, since they are capable of intercalating into double-stranded DNA and are inhibitors of topoisomerase II (Topo II). Many 9-anilinoacridine derivatives and their structure-activity relationships have been reported; see, for examples, Atwell et al., *J. Med. Chem.* 1972, 15:611; Cain et al., *J. Med. Chem.* 1974, 17:922; Cain et al., *J. Med. Chem.* 1975, 18:1110; and Rewcastle et al., *J. Med. Chem.* 1986, 29:472. Among these compounds, m-amsacrine [4'-(9-acridinylamino)methanesulfon-m-anisidine, m-AMSA] and its 5-methyl-4-methylcarboxamide derivative (known as CI-921) were of particular interest. Cain et al., *Eur. J. Cancer* 1974, 10:539 and Arlin Z., *Cancer Treat. Rep.* 1983, 967 reported the clinical use of m-AMSA for the treatment of acute leukemia. Baguley et al., *Cancer Res.* 1984, 44:3245 and Denny et al., *J. Med. Chem.* 1987, 30:658 described the phase II trials of CI-921 for treatment of leukemia and solid tumors. The antitumor activity of m-AMSA is attributed to Topo II-mediated cleavage of double-stranded DNA, by a mechanism which appears to be common to DNA-intercalating agents; see, for examples, Nelson et al., *Proc. Natl. Acad. Sci. USA*, 1984, 81:1364 and Pommier et al., *Cancer Res.* 1985, 41:3143.

Both m-AMSA and CI-921 possess a methanesulfonyl and a methoxyl function at C-1' and C-3' of the anilino ring and readily undergo reversible oxidation chemically or microsomally giving the quinonediimine (m-AQDI); see, for example, Shoemaker et al, *Cancer Res.* 1984, 44:1939 and Shoemaker et al., *Drug Metab. Dispos.* 1982, 10:35. When mouse and rat were treated with m-AMSA, the major biliary metabolites of this agent were the 5'- and 6'-glutathione (GSH) conjugates, with no C9-GSH conjugate being found; see for example, Shoemaker et al, *Cancer Res.* 1984, 44:1939, supra; Shoemaker et al., *Drug Metab. Dispos.* 1982, 10:35, supra; Robertson et al., *Drug Metab. Drug Interact.* 1988, 6:371; and Robertson et al., *Xenobiotica* 1992, 22:657. In the case of CI-921, in addition to the 5'- and 6'-GSH conjugates, two other metabolites, namely C9-GSH and the 4-hydroxymethyl derivatives of CI-921, were detected (Robertson et al., *Xenobiotica* 1992, 22:657, supra). More than 50% of the dose was excreted as the glutathione conjugate in the bile when the mouse was treated with these two drugs. The half-life of m-AMSA in the presence of fresh mouse blood at 37° C. is ca. 30 min. See, for example, Shoemaker *Drug Metab. Dispos.* 1982, 10:35 supra and Robertson et al., *Drug Metab., Drug Interact.* 1988, 6:371, supra.

Chou et al., *Am. Assoc. Cancer Res.* 1994, 368 recently reported a series of 9-anilinoacridine analogues in which the 9-amino was substituted by an O or S atom or compounds lacking the substituent at the para position of the 9-amino function of acridine. These new series of compounds are incapable of forming diiminoquinone intermediate by oxidation and are, therefore, expected to have longer duration of drug action with higher chemotherapeutic effect. Among these compounds, 3-(acridin-9-yl)amino-5-hydroxymethylaniline (AHMA) was shown to have significant antitumor activity both in vitro and in vivo. The preliminary antitumor efficacy of AHMA and its derivatives indicated that 1) AHMA and its derivatives represent a novel type of antitumor agents which have a longer plasma half-life (1.5 h) than m-AMSA; and 2) AHMA has greater efficacy against murine leukemia and solid tumors (a mammary adenocarcinoma, B-16 melanoma and Lewis lung carcinoma) than m-AMSA and VP-16, and yet is less toxic toward the host.

Su et al., *Journal of Medicinal Chemistry,* 1995, 38:17 disclosed N-(tert-butoxycarbonyl)-3-(9-acridinylamino)-5-(hydroxymethyl)aniline as an intermediate for preparing 3-(9-acridinylamino)-5-aminobenzyl N-methylcarbamate. However, the pharmacological activity of the intermediate were not described therein.

We have surprisingly found that the N-alkoxycarbonyl derivatives of AHMA, i.e. the alkyl N-[3-(acridin-9-yl)amino-5-hydroxy-methyl]phenylcarbamate derivatives, possess even better antitumor efficacy in vitro and in vivo than their precursor, AHMA (Tables 1 and 2, infra).

SUMMARY OF THE INVENTION

Accordingly, the present invention provides compounds of Formula (I):

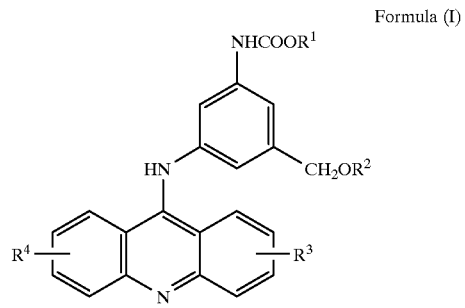

Formula (I)

wherein
$R^1$ is $C_{1-6}$ alkyl; or phenyl;
$R^2$ is hydrogen;
  an acyl group of the formula —$COR^a$ wherein $R^a$ is $C_{1-6}$ alkyl or phenyl; or
  an acetylalkylcarbonyl group of the formula —$CO(CH_2)_nCOCH_3$ wherein n=1–3; and
$R^3$ and $R^4$ are substituents at different position(s) of the acridine ring (i.e. C-1'–C-8'), and $R^3$ and $R^4$ may be the same or different and independently represent:
  hydrogen;
  $C_{1-6}$ alkyl;
  $C_{1-6}$ alkyloxy;
  a nitro group;
  an amino group of the formula —$NR^bR^c$ wherein $R^b$ and $R^c$ may be the same or different and independently represent hydrogen or $C_{1-6}$ alkyl;
  an aminoalkylamino group of the formula —$NH(CH_2)_nNR^dR^e$ wherein $R^d$ and $R^e$ may be the same or different and independently represent hydrogen, $C_{1-6}$ alkyl, a hydroxyalkyl group of the formula —$(CH_2)_nOH$ wherein n=1–3, or $C_{1-6}$ haloalkyl;

an alkylaminocarbonyl group of the formula —CONHR$^f$ wherein R$^f$ is C$_{1-6}$ alkyl;

an alkylaminoalkylaminocarbonyl group of the formula —CONH(CH$_2$)$_n$NR$^g$R$^h$ wherein n=1–5, and R$^g$ and R$^h$ may be the same or different and independently represent hydrogen, C$_{1-6}$ alkyl, or a nitro group;

a halogen group;

a hydroxyalkyl group of the formula —(CH$_2$)$_n$OH wherein n=1–3;

a carbamate group of the formula —CH$_2$CONHR$^f$ wherein R$^f$ is as defined above;

an alkylcarbonyloxymethyl group of the formula —CH$_2$OCOR$^f$ wherein R$^f$ is as defined above;

an alkyl sulfonate of the formula —SO$_3$R$^f$ wherein R$^f$ is as defined above; and an alkylsulfonyl group of the formula —SO$_2$R$^f$ wherein R$^f$ is as defined above;

with the proviso that when R$^2$, R$^3$ and R$^4$ are hydrogen, R$^1$ is not t-butyl;

and the pharmaceutically acceptable salts thereof.

The present invention also provides a process for synthesizing the compounds of Formula (I) which comprises:

(a) condensing mono-, di- or multi-substituted 9-chloroacridines with 3,5-diaminobenzyl alcohol dihydrochloride under suitable conditions to form mono-, di-, or multi-substituted 3-(acridin-9-yl)amino-5-hydroxymethylanilines of Formula (II):

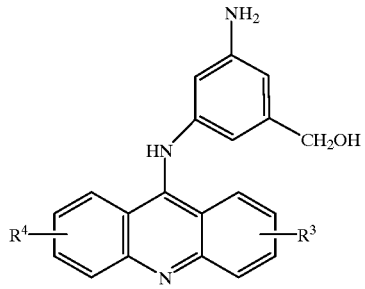

Formula (II)

wherein R$^3$ and R$^4$ are as defined above;

(b) treating the compounds of Formula (II) with a haloformate of the formula XCOOR$^i$ wherein X is a halogen and R$^i$ is C$_{1-6}$ alkyl or optionally substituted phenyl under suitable conditions to form the compounds of Formula (I) wherein R$^2$ is hydrogen;

(c) if desired, O-acylating the compounds of Formula (I) wherein R$^2$ is hydrogen under suitable conditions to form the compounds of Formula (I) wherein R$^2$ is an acyl group of the formula —COR$^a$ wherein R$^a$ is C$_{1-6}$ alkyl or phenyl; or R$^2$ is an acetylalkylcarbonyl group of the formula —CO(CH$_2$)$_n$COCH$_3$ wherein n=1–3; and (d) if desired, converting the compounds of Formula (I) into the pharmaceutically salts thereof as appropriate.

Most of the intermediates of Formula (II) formed in step (b) are novel compounds. Accordingly, the present invention also provides novel compounds of Formula (II)

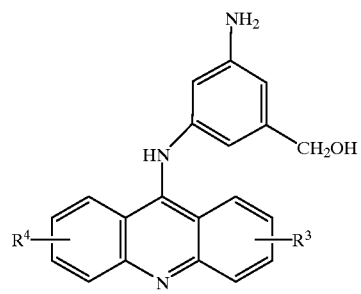

Formula (II)

wherein R$^3$ and R$^4$ are as defined above;
with the proviso that at least one of R$^3$ and R$^4$ is not hydrogen;
and the pharmaceutically acceptable salts thereof.

The present invention also provides a pharmaceutical composition which comprises as the active ingredient an effective amount of a compound of Formula (I):

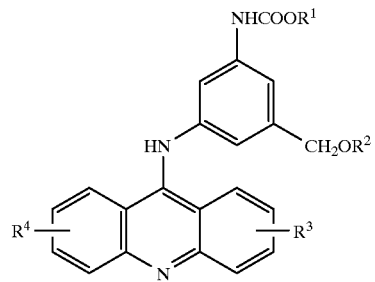

Formula (I)

wherein
R$^1$ is C$_{1-6}$ alkyl; or phenyl;
R$^2$ is hydrogen;
an acyl group of the formula —COR$^a$ wherein R$^a$ is C$_{1-6}$ alkyl or phenyl; or
an acetylalkylcarbonyl group of the formula —CO(CH$_2$)$_n$COCH$_3$ wherein n=1–3; and
R$^3$ and R$^4$ are substituents at different position(s) of the acridine ring (i.e. C-1'–C-8'), and R$^3$ and R$^4$ may be the same or different and independently represent:
hydrogen;
C$_{1-6}$ alkyl;
C$_{1-6}$ alkyloxy;
a nitro group;
an amino group of the formula —NR$^b$R$^c$ wherein R$^b$ and R$^c$ may be the same or different and independently represent hydrogen or C$_{1-6}$ alkyl;
an aminoalkylamino group of the formula —NH(CH$_2$)$_n$NR$^d$R$^e$ wherein R$^d$ and R$^e$ may be the same or different and independently represent hydrogen, C$_{1-6}$ alkyl, a hydroxyalkyl group of the formula —(CH$_2$)$_n$OH wherein n=1–3, or C$_{1-6}$ haloalkyl;
an alkylaminocarbonyl group of the formula —CONHR$^f$ wherein R$^f$ is C$_{1-6}$ alkyl;
an alkylaminoalkylaminocarbonyl group of the formula —CONH(CH$_2$)$_n$NR$^g$R$^h$ wherein n=1–5, and R$^g$ and R$^h$ may be the same or different and independently represent hydrogen, C$_{1-6}$ alkyl, or a nitro group;
a halogen group;
a hydroxyalkyl group of the formula —(CH$_2$)$_n$OH wherein n=1–3;

a carbamate group of the formula —CH$_2$CONHR$^f$ wherein R$^f$ is as defined above;

an alkylcarbonyloxymethyl group of the formula —CH$_2$OCOR$^f$ wherein R$^f$ is as defined above;

an alkyl sulfonate of the formula —SO$_3$R$^f$ wherein R$^f$ is as defined above; and an alkylsulfonyl group of the formula —SO$_2$R$^f$ wherein R$^f$ is as defined above;

and the pharmaceutically acceptable salts thereof; in combination with a pharmaceutically acceptable carrier thereof.

The present invention also provides a pharmaceutical composition which comprises as the active ingredient an effective amount of the novel compound of Formula (II) as described above and a pharmaceutically acceptable carrier thereof.

The present invention also provides the use of the compounds of Formula (I) and of the novel compounds of Formula (II) for treating diseases. In particular, the invention provides the use of the above compounds for inhibiting growth of tumor cells.

The invention also provides methods of treating diseases. In particular, the invention provides methods of inhibiting growth of tumor cells which comprises contacting the tumor cells with an effective amount of the compounds of Formula (I) or the novel compounds of Formula (II).

DETAILED DESCRIPTION OF THE INVENTION

In the broadest scope, the present invention provides the compounds of Formula (I):

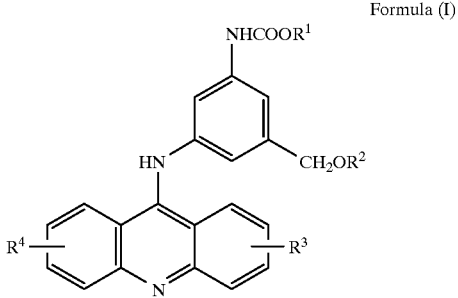

Formula (I)

wherein

R$^1$ is C$_{1-6}$ alkyl; or phenyl;

R$^2$ is hydrogen;
   an acyl group of the formula —COR$^a$ wherein R$^a$ is C$_{1-6}$ alkyl or phenyl; or
   an acetylalkylcarbonyl group of the formula —CO(CH$_2$)$_n$COCH$_3$ wherein n=1–3; and R$^3$ and R$^4$ are substituents at different position(s) of the acridine ring (i.e. C-1'–C-8'), and R$^3$ and R$^4$ may be the same or different and independently represent:
   hydrogen;
   C$_{1-6}$ alkyl;
   C$_{1-6}$ alkyloxy;
   a nitro group;
   an amino group of the formula —NR$^b$R$^c$ wherein R$^b$ and R$^c$ may be the same or different and independently represent hydrogen or C$_{1-6}$ alkyl;
   an aminoalkylamino group of the formula —NH(CH$_2$)$_n$NR$^d$R$^e$ wherein R$^d$ and R$^e$ may be the same or different and independently represent hydrogen, C$_{1-6}$ alkyl, a hydroxyalkyl group of the formula —(CH$_2$)$_n$OH wherein n=1–3, or C$_{1-6}$ haloalkyl;
   an alkylaminocarbonyl group of the formula —CONHR$^f$ wherein R$^f$ is C$_{1-6}$ alkyl;
   an alkylaminoalkylaminocarbonyl group of the formula —CONH(CH$_2$)$_n$NR$^g$R$^h$ wherein n=1–5, and R$^g$ and R$^h$ may be the same or different and independently represent hydrogen, C$_{1-6}$ alkyl, or a nitro group;
   a halogen group;
   a hydroxyalkyl group of the formula —(CH$_2$)$_n$OH wherein n=1–3;
   a carbamate group of the formula —CH$_2$CONHR$^f$ wherein R$^f$ is as defined above;
   an alkylcarbonyloxymethyl group of the formula —CH$_2$OCOR$^f$ wherein R$^f$ is as defined above;
   an alkyl sulfonate of the formula —SO$_3$R$^f$ wherein R$^f$ is as defined above; and
   an alkylsulfonyl group of the formula —SO$_2$R$^f$ wherein R$^f$ is as defined above;

with the proviso that when R$^2$, R$^3$ and R$^4$ are hydrogen, R$^1$ is not t-butyl;

and the pharmaceutically acceptable salts thereof.

The term "C$_{1-6}$ alkyl" used herein refers to a linear or branched alkyl group containing 1–6 carbon atoms, including but not limited to methyl, ethyl, n-propyl, i-propyl, n-butyl, and t-butyl.

The term "C$_{1-6}$ alkyloxy" used herein refers to a linear or branched alkyloxy group containing 1–6 carbon atoms, including but not limited to methoxy, ethoxy, propoxy, butoxy, sec-butoxy and tert-butoxy.

The term "halogen" or the "halo" moiety in a radical herein refers to a halogen atom such as fluoro, chloro, bromo and iodo. Accordingly, a haloalkyl group may include fluoroalkyl and chloroalkyl such as trifluoromethyl and chloroethyl.

For illustrative purpose, the compounds of Formula (I) may be selected from, but are not limited to, the group consisting of:

methyl N-[3-(acridin-9-yl)amino-5-hydroxymethyl]phenylcarbamate;

ethyl N-[3-(acridin-9-yl)amino-5-hydroxymethyl]phenylcarbamate;

n-propyl N-[3-(acridin-9-yl)amino-5-hydroxymethyl]phenylcarbamate;

i-propyl N-[3-(acridin-9-yl)amino-5-hydroxymethyl]phenylcarbamate;

n-butyl N-[3-(acridin-9-yl)amino-5-hydroxymethyl]phenylcarbamate;

i-butyl N-[3-(acridin-9-yl)amino-5-hydroxymethyl]phenylcarbamate;

phenyl N-[3-(acridin-9-yl)amino-5-hydroxymethyl]phenylcarbamate;

methyl N-[3-(3-methylacridin-9-yl)amino-5-hydroxymethyl]phenylcarbamate;

ethyl N-[3-(3-methylacridin-9-yl)amino-5-hydroxymethyl]phenylcarbamate;

n-propyl N-[3-(3-methylacridin-9-yl)amino-5-hydroxymethyl]phenylcarbamate;

i-propyl N-[3-(3-methylacridin-9-yl)amino-5-hydroxymethyl]phenylcarbamate;

n-butyl N-[3-(3-methylacridin-9-yl)amino-5-hydroxymethyl]phenylcarbamate;

i-butyl N-[3-(3-methylacridin-9-yl)amino-5-hydroxymethyl]phenylcarbamate;

t-butyl N-[3-(3-methylacridin-9-yl)amino-5-hydroxymethyl]phenylcarbamate;

phenyl N-[3-(3-methylacridin-9-yl)amino-5-hydroxymethyl]phenylcarbamate;

methyl N-[3-(4-methylacridin-9-yl)amino-5-hydroxymethyl]phenylcarbamate;

ethyl N-[3-(4-methylacridin-9-yl)amino-5-hydroxymethyl] phenylcarbamate;
n-propyl N-[3-(4-methylacridin-9-yl)amino-5-hydroxymethyl]phenylcarbamate;
i-propyl N-[3-(4-methylacridin-9-yl)amino-5-hydroxymethyl]phenylcarbamate;
n-butyl N-[3-(4-methylacridin-9-yl)amino-5-hydroxymethyl]phenylcarbamate;
i-butyl N-[3-(4-methylacridin-9-yl)amino-5-hydroxymethyl]phenylcarbamate;
t-butyl N-[3-(4-methylacridin-9-yl)amino-5-hydroxymethyl]phenylcarbamate;
phenyl N-[3-(4-methylacridin-9-yl)amino-5-hydroxymethyl]phenylcarbamate;
methyl N-[3-(3-nitroacridin-9-yl)amino-5-hydroxymethyl] phenylcarbamate;
ethyl N-[3-(3-nitroacridin-9-yl)amino-5-hydroxymethyl] phenylcarbamate;
n-propyl N-[3-(3-nitroacridin-9-yl)amino-5-hydroxymethyl]phenylcarbamate;
i-propyl N-[3-(3-nitroacridin-9-yl)amino-5-hydroxymethyl] phenylcarbamate;
n-butyl N-[3-(3-nitroacridin-9-yl)amino-5-hydroxymethyl] phenylcarbamate;
i-butyl N-[3-(3-nitroacridin-9-yl)amino-5-hydroxymethyl] phenylcarbamate;
t-butyl N-[3-(3-nitroacridin-9-yl)amino-5-hydroxymethyl] phenylcarbamate;
phenyl N-[3-(3-nitroacridin-9-yl)amino-5-hydroxymethyl] phenylcarbamate;
methyl N-[3-(4-nitroacridin-9-yl)amino-5-hydroxymethyl] phenylcarbamate;
ethyl N-[3-(4-nitroacridin-9-yl)amino-5-hydroxymethyl] phenylcarbamate;
n-propyl N-[3-(4-nitroacridin-9-yl)amino-5-hydroxymethyl]phenylcarbamate;
i-propyl N-[3-(4-nitroacridin-9-yl)amino-5-hydroxymethyl] phenylcarbamate;
n-butyl N-[3-(4-nitroacridin-9-yl)amino-5-hydroxymethyl] phenylcarbamate;
i-butyl N-[3-(4-nitroacridin-9-yl)amino-5-hydroxymethyl] phenylcarbamate;
t-butyl N-[3-(4-nitroacridin-9-yl)amino-5-hydroxymethyl] phenylcarbamate;
phenyl N-[3-(4-nitroacridin-9-yl)amino-5-hydroxymethyl] phenylcarbamate;
methyl N-[3-(3-aminoacridin-9-yl)amino-5-hydroxymethyl]phenylcarbamate;
ethyl N-[3-(3-aminoacridin-9-yl)amino-5-hydroxymethyl] phenylcarbamate;
n-propyl N-[3-(3-aminoacridin-9-yl)amino-5-hydroxymethyl]phenylcarbamate;
i-propyl N-[3-(3-aminoacridin-9-yl)amino-5-hydroxymethyl]phenylcarbamate;
n-butyl N-[3-(3-aminoacridin-9-yl)amino-5-hydroxymethyl]phenylcarbamate;
i-butyl N-[3-(3-aminoacridin-9-yl)amino-5-hydroxymethyl] phenylcarbamate;
t-butyl N-[3-(3-aminoacridin-9-yl)amino-5-hydroxymethyl] phenylcarbamate;
phenyl N-[3-(3-aminoacridin-9-yl)amino-5-hydroxymethyl] phenylcarbamate;
methyl N-[3-(4-aminoacridin-9-yl)amino-5-hydroxymethyl]phenylcarbamate;
ethyl N-[3-(4-aminoacridin-9-yl)amino-5-hydroxymethyl] phenylcarbamate;
n-propyl N-[3-(4-aminoacridin-9-yl)amino-5-hydroxymethyl]phenylcarbamate;
i-propyl N-[3-(4-aminoacridin-9-yl)amino-5-hydroxymethyl]phenylcarbamate;
n-butyl N-[3-(4-aminoacridin-9-yl)amino-5-hydroxymethyl]phenylcarbamate;
i-butyl N-[3-(4-aminoacridin-9-yl)amino-5-hydroxymethyl] phenylcarbamate;
t-butyl N-[3-(4-aminoacridin-9-yl)amino-5-hydroxymethyl] phenylcarbamate;
phenyl N-[3-(4-aminoacridin-9-yl)amino-5-hydroxymethyl] phenylcarbamate;
methyl N-[3-(3-methylaminoacridin-9-yl)amino-5-hydroxymethyl]phenylcarbamate;
ethyl N-[3-(3-methylaminoacridin-9-yl)amino-5-hydroxymethyl]phenylcarbamate;
n-propyl N-[3-(3-methylaminoacridin-9-yl)amino-5-hydroxymethyl]phenylcarbamate;
i-propyl N-[3-(3-methylaminoacridin-9-yl)amino-5-hydroxymethyl]phenylcarbamate;
n-butyl N-[3-(3-methylaminoacridin-9-yl)amino-5-hydroxymethyl]phenylcarbamate;
i-butyl N-[3-(3-methylaminoacridin-9-yl)amino-5-hydroxymethyl]phenylcarbamate;
t-butyl N-[3-(3-methylaminoacridin-9-yl)amino-5-hydroxymethyl]phenylcarbamate;
phenyl N-[3-(3-methylaminoacridin-9-yl)amino-5-hydroxymethyl]phenylcarbamate;
methyl N-[3-(4-methylaminoacridin-9-yl)amino-5-hydroxymethyl]phenylcarbamate;
ethyl N-[3-(4-methylaminoacridin-9-yl)amino-5-hydroxymethyl]phenylcarbamate;
n-propyl N-[3-(4-methylaminoacridin-9-yl)amino-5-hydroxymethyl]phenylcarbamate;
i-propyl N-[3-(4-methylaminoacridin-9-yl)amino-5-hydroxymethyl]phenylcarbamate;
n-butyl N-[3-(4-methylaminoacridin-9-yl)amino-5-hydroxymethyl]phenylcarbamate;
i-butyl N-[3-(4-methylaminoacridin-9-yl)amino-5-hydroxymethyl]phenylcarbamate;
t-butyl N-[3-(4-methylaminoacridin-9-yl)amino-5-hydroxymethyl]phenylcarbamate;
phenyl N-[3-4(-methylaminoacridin-9-yl)amino-5-hydroxymethyl]phenylcarbamate;
methyl N-[3-(3-N,N-dimethylaminoacridin-9-yl)amino-5-hydroxymethyl]phenylcarbamate;
ethyl N-[3-(3-N,N-dimethylaminoacridin-9-yl)amino-5-hydroxymethyl]phenylcarbamate;
n-propyl N-[3-(3-N,N-dimethylaminoacridin-9-yl)amino-5-hydroxymethyl]phenylcarbamate;
i-propyl N-[3-(3-N,N-dimethylaminoacridin-9-yl)amino-5-hydroxymethyl]phenylcarbamate;
n-butyl N-[3-(3-N,N-dimethylaminoacridin-9-yl)amino-5-hydroxymethyl]phenylcarbamate;
i-butyl N-[3-(3-N,N-dimethylaminoacridin-9-yl)amino-5-hydroxymethyl]phenylcarbamate;
t-butyl N-[3-(3-N,N-dimethylaminoacridin-9-yl)amino-5-hydroxymethyl]phenylcarbamate;
phenyl N-[3-(3-N,N-dimethylaminoacridin-9-yl)amino-5-hydroxymethyl]phenylcarbamate;
methyl N-[3-(4-N,N-dimethylaminoacridin-9-yl)amino-5-hydroxymethyl]phenylcarbamate;
ethyl N-[3-(4-N,N-dimethylaminoacridin-9-yl)amino-5-hydroxymethyl]phenylcarbamate;
n-propyl N-[3-(4-N,N-dimethylaminoacridin-9-yl)amino-5-hydroxymethyl]phenylcarbamate;
i-propyl N-[3-(4-N,N-dimethylaminoacridin-9-yl)amino-5-hydroxymethyl]phenylcarbamate;
n-butyl N-[3-(4-N,N-dimethylaminoacridin-9-yl)amino-5-hydroxymethyl]phenylcarbamate;

i-butyl N-[3-(4-N,N-dimethylaminoacridin-9-yl)amino-5-hydroxymethyl]phenylcarbamate;
t-butyl N-[3-(4-N,N-dimethylaminoacridin-9-yl)amino-5-hydroxymethyl]phenylcarbamate;
phenyl N-[3-(4-N,N-dimethylaminoacridin-9-yl)amino-5-hydroxymethyl]phenylcarbamate;
methyl N-[3-(3-hydroxycarbonylacridin-9-yl)amino-5-hydroxymethyl]phenylcarbamate;
ethyl N-[3-(3-hydroxycarbonylacridin-9-yl)amino-5-hydroxymethyl]phenylcarbamate;
n-propyl N-[3-(3-hydroxycarbonylacridin-9-yl)amino-5-hydroxymethyl]phenylcarbamate;
i-propyl N-[3-(3-hydroxycarbonylacridin-9-yl)amino-5-hydroxymethyl]phenylcarbamate;
n-butyl N-[3-(3-hydroxycarbonylacridin-9-yl)amino-5-hydroxymethyl]phenylcarbamate;
i-butyl N-[3-(3-hydroxycarbonylacridin-9-yl)amino-5-hydroxymethyl]phenylcarbamate;
t-butyl N-[3-(3-hydroxycarbonylacridin-9-yl)amino-5-hydroxymethyl]phenylcarbamate;
phenyl N-[3-(3-hydroxycarbonylacridin-9-yl)amino-5-hydroxymethyl]phenylcarbamate;
methyl N-[3-(4-hydroxycarbonylacridin-9-yl)amino-5-hydroxymethyl]phenylcarbamate;
ethyl N-[3-(4-hydroxycarbonylacridin-9-yl)amino-5-hydroxymethyl]phenylcarbamate;
n-propyl N-[3-(4-hydroxycarbonylacridin-9-yl)amino-5-hydroxymethyl]phenylcarbamate;
i-propyl N-[3-(4-hydroxycarbonylacridin-9-yl)amino-5-hydroxymethyl]phenylcarbamate;
n-butyl N-[3-(4-hydroxycarbonylacridin-9-yl)amino-5-hydroxymethyl]phenylcarbamate;
i-butyl N-[3-(4-hydroxycarbonylacridin-9-yl)amino-5-hydroxymethyl]phenylcarbamate;
t-butyl N-[3-(4-hydroxycarbonylacridin-9-yl)amino-5-hydroxymethyl]phenylcarbamate;
phenyl N-[3-(4-hydroxycarbonylacridin-9-yl)amino-5-hydroxymethyl]phenylcarbamate;
methyl N-[3-(3-methoxycarbonylacridin-9-yl)amino-5-hydroxymethyl]phenylcarbamate;
ethyl N-[3-(3-methoxycarbonylacridin-9-yl)amino-5-hydroxymethyl]phenylcarbamate;
n-propyl N-[3-(3-methoxycarbonylacridin-9-yl)amino-5-hydroxymethyl]phenylcarbamate;
i-propyl N-[3-(3-methoxycarbonylacridin-9-yl)amino-5-hydroxymethyl]phenylcarbamate;
n-butyl N-[3-(3-methoxycarbonylacridin-9-yl)amino-5-hydroxymethyl]phenylcarbamate;
i-butyl N-[3-(3-methoxycarbonylacridin-9-yl)amino-5-hydroxymethyl]phenylcarbamate;
t-butyl N-[3-(3-methoxycarbonylacridin-9-yl)amino-5-hydroxymethyl]phenylcarbamate;
phenyl N-[3-(3-methoxycarbonylacridin-9-yl)amino-5-hydroxymethyl]phenylcarbamate;
methyl N-[3-(4-methoxycarbonylacridin-9-yl)amino-5-hydroxymethyl]phenylcarbamate;
ethyl N-[3-(4-methoxycarbonylacridin-9-yl)amino-5-hydroxymethyl]phenylcarbamate;
n-propyl N-[3-(4-methoxycarbonylacridin-9-yl)amino-5-hydroxymethyl]phenylcarbamate;
i-propyl N-[3-(4-methoxycarbonylacridin-9-yl)amino-5-hydroxymethyl]phenylcarbamate;
n-butyl N-[3-(4-methoxycarbonylacridin-9-yl)amino-5-hydroxymethyl]phenylcarbamate;
i-butyl N-[3-(4-methoxycarbonylacridin-9-yl)amino-5-hydroxymethyl]phenylcarbamate;
t-butyl N-[3-(4-methoxycarbonylacridin-9-yl)amino-5-hydroxymethyl]phenylcarbamate;
phenyl N-[3-(4-methoxycarbonylacridin-9-yl)amino-5-hydroxymethyl]phenylcarbamate;
methyl N-[3-(3-aminocarbonylacridin-9-yl)amino-5-hydroxymethyl]-phenylcarbamate;
ethyl N-[3-(3-aminocarbonylacridin-9-yl)amino-5-hydroxymethyl]-phenylcarbamate;
n-propyl N-[3-(3-aminocarbonylacridin-9-yl)amino-5-hydroxymethyl]phenylcarbamate;
1-propyl N-[3-(3-aminocarbonylacridin-9-yl)amino-5-hydroxymethyl]phenylcarbamate;
n-butyl N-[3-(3-aminocarbonylacridin-9-yl)amino-5-hydroxymethyl]phenylcarbamate;
i-butyl N-[3-(3-aminocarbonylacridin-9-yl)amino-5-hydroxymethyl]phenylcarbamate;
t-butyl N-[3-(3-aminocarbonylacridin-9-yl)amino-5-hydroxymethyl]phenylcarbamate;
phenyl N-[3-(3-aminocarbonylacridin-9-yl)amino-5-hydroxymethyl]phenylcarbamate;
methyl N-[3-(4-aminocarbonylacridin-9-yl)amino-5-hydroxymethyl]phenylcarbamate;
ethyl N-[3-(4-aminocarbonylacridin-9-yl)amino-5-hydroxymethyl]phenylcarbamate;
n-propyl N-[3-(4-aminocarbonylacridin-9-yl)amino-5-hydroxymethyl]phenylcarbamate;
i-propyl N-[3-(4-aminocarbonylacridin-9-yl)amino-5-hydroxymethyl]phenylcarbamate;
n-butyl N-[3-(4-aminocarbonylacridin-9-yl)amino-5-hydroxymethyl]phenylcarbamate;
i-butyl N-[3-(4-aminocarbonylacridin-9-yl)amino-5-hydroxymethyl]phenylcarbamate;
t-butyl N-[3-(4-aminocarbonylacridin-9-yl)amino-5-hydroxymethyl]phenylcarbamate;
phenyl N-[3-(4-aminocarbonylacridin-9-yl)amino-5-hydroxymethyl]phenylcarbamate;
methyl N-[3-(3-methylaminocarbonylacridin-9-yl)amino-5-hydroxymethyl]phenylcarbamate;
ethyl N-[3-(3-methylaminocarbonylacridin-9-yl)amino-5-hydroxymethyl]phenylcarbamate;
n-propyl N-[3-(3-methylaminocarbonylacridin-9-yl)amino-5-hydroxymethyl]phenylcarbamate;
i-propyl N-[3-(3-methylaminocarbonylacridin-9-yl)amino-5-hydroxymethyl]phenylcarbamate;
n-butyl N-[3-(3-methylaminocarbonylacridin-9-yl)amino-5-hydroxymethyl]phenylcarbamate;
i-butyl N-[3-(3-methylaminocarbonylacridin-9-yl)amino-5-hydroxymethyl]phenylcarbamate;
t-butyl N-[3-(3-methylaminocarbonylacridin-9-yl)amino-5-hydroxymethyl]phenylcarbamate;
phenyl N-[3-(3-methylaminocarbonylacridin-9-yl)amino-5-hydroxymethyl]phenylcarbamate;
methyl N-[3-(4-methylaminocarbonylacridin-9-yl)amino-5-hydroxymethyl]phenylcarbamate;
ethyl N-[3-(4-methylaminocarbonylacridin-9-yl)amino-5-hydroxymethyl]phenylcarbamate;
n-propyl N-[3-(4-methylaminocarbonylacridin-9-yl)amino-5-hydroxymethyl]phenylcarbamate;
i-propyl N-[3-(4-methylaminocarbonylacridin-9-yl)amino-5-hydroxymethyl]phenylcarbamate;
n-butyl N-[3-(4-methylaminocarbonylacridin-9-yl)amino-5-hydroxymethyl]phenylcarbamate;
i-butyl N-[3-(4-methylaminocarbonylacridin-9-yl)amino-5-hydroxymethyl]phenylcarbamate;
t-butyl N-[3-(4-methylaminocarbonylacridin-9-yl)amino-5-hydroxymethyl]phenylcarbamate;
phenyl N-[3-(4-methylaminocarbonylacridin-9-yl)amino-5-hydroxymethyl]phenylcarbamate;
methyl N-[3-(3-N,N-dimethylaminocarbonylacridin-9-yl)amino-5-hydroxymethyl]phenylcarbamate;

ethyl N-[3-(3-N,N-dimethylaminocarbonylacridin-9-yl) amino-5-hydroxymethyl]phenylcarbamate;
n-propyl N-[3-(3-N,N-dimethylaminocarbonylacridin-9-yl) amino-5-hydroxymethyl]phenylcarbamate;
i-propyl N-[3-(3-N,N-dimethylaminocarbonylacridin-9-yl) amino-5-hydroxymethyl]phenylcarbamate;
n-butyl N-[3-(3-N,N-dimethylaminocarbonylacridin-9-yl) amino-5-hydroxymethyl]phenylcarbamate;
i-butyl N-[3-(3-N,N-dimethylaminocarbonylacridin-9-yl) amino-5-hydroxymethyl]phenylcarbamate;
t-butyl N-[3-(3-N,N-dimethylaminocarbonylacridin-9-yl) amino-5-hydroxymethyl]phenylcarbamate;
phenyl N-[3-(3-N,N-dimethylaminocarbonylacridin-9-yl) amino-5-hydroxymethyl]phenylcarbamate;
methyl N-[3-(4-N,N-dimethylaminocarbonylacridin-9-yl) amino-5-hydroxymethyl phenylcarbamate;
ethyl N-[3-(4-N,N-dimethylaminocarbonylacridin-9-yl) amino-5-hydroxymethyl]phenylcarbamate;
n-propyl N-[3-(4-N,N-dimethylaminocarbonylacridin-9-yl) amino-5-hydroxymethyl]phenylcarbamate;
i-propyl N-[3-(4-N,N-dimethylaminocarbonylacridin-9-yl) amino-5-hydroxymethyl]phenylcarbamate;
n-butyl N-[3-(4-N,N-dimethylaminocarbonylacridin-9-yl) amino-5-hydroxymethyl]phenylcarbamate;
i-butyl N-[3-(4-N,N-dimethylaminocarbonylacridin-9-yl) amino-5-hydroxymethyl]phenylcarbamate;
t-butyl N-[3-(4-N,N-dimethylaminocarbonylacridin-9-yl) amino-5-hydroxymethyl]phenylcarbamate;
phenyl N-[3-(4-N,N-dimethylaminocarbonylacridin-9-yl) amino-5-hydroxymethyl]phenylcarbamate;
methyl N-[3-(3-methoxyacridin-9-yl)amino-5-hydroxymethyl]phenylcarbamate;
ethyl N-[3-(3-methoxyacridin-9-yl)amino-5-hydroxymethyl]phenylcarbamate;
n-propyl N-[3-(3-methoxyacridin-9-yl)amino-5-hydroxymethyl]phenylcarbamate;
i-propyl N-[3-(3-methoxyacridin-9-yl)amino-5-hydroxymethyl]phenylcarbamate;
n-butyl N-[3-(3-methoxyacridin-9-yl)amino-5-hydroxymethyl]phenylcarbamate;
i-butyl N-[3-(3-methoxyacridin-9-yl)amino-5-hydroxymethyl]phenylcarbamate;
t-butyl N-[3-(3-methoxyacridin-9-yl)amino-5-hydroxymethyl]phenylcarbamate;
phenyl N-[3-(3-methoxyacridin-9-yl)amino-5-hydroxymethyl]phenylcarbamate;
methyl N-[3-(4-methoxyacridin-9-yl)amino-5-hydroxymethyl]phenylcarbamate;
ethyl N-[3-(4-methoxyacridin-9-yl)amino-5-hydroxymethyl]phenylcarbamate;
n-propyl N-[3-(4-methoxyacridin-9-yl)amino-5-hydroxymethyl]phenylcarbamate;
i-propyl N-[3-(4-methoxyacridin-9-yl)amino-5-hydroxymethyl]phenylcarbamate;
n-butyl N-[3-(4-methoxyacridin-9-yl)amino-5-hydroxymethyl]phenylcarbamate;
i-butyl N-[3-(4-methoxyacridin-9-yl)amino-5-hydroxymethyl]phenylcarbamate;
t-butyl N-[3-(4-methoxyacridin-9-yl)amino-5-hydroxymethyl]phenylcarbamate;
phenyl N-[3-(4-methoxyacridin-9-yl)amino-5-hydroxymethyl]phenylcarbamate;
methyl N-[3-(3-chloroacridin-9-yl)amino-5-hydroxymethyl]phenylcarbamate;
ethyl N-[3-(3-chloroacridin-9-yl)amino-5-hydroxymethyl]phenylcarbamate;
n-propyl N-[3-(3-chloroacridin-9-yl)amino-5-hydroxymethyl]phenylcarbamate;
i-propyl N-[3-(3-chloroacridin-9-yl)amino-5-hydroxymethyl]phenylcarbamate;
n-butyl N-[3-(3-chloroacridin-9-yl)amino-5-hydroxymethyl]phenylcarbamate;
i-butyl N-[3-(3-chloroacridin-9-yl)amino-5-hydroxymethyl]phenylcarbamate;
t-butyl N-[3-(3-chloroacridin-9-yl)amino-5-hydroxymethyl]phenylcarbamate;
phenyl N-[3-(3-chloroacridin-9-yl)amino-5-hydroxymethyl]phenylcarbamate;
methyl N-[3-(4-chloroacridin-9-yl)amino-5-hydroxymethyl]phenylcarbamate;
ethyl N-[3-(4-chloroacridin-9-yl)amino-5-hydroxymethyl]phenylcarbamate;
n-propyl N-[3-(4-chloroacridin-9-yl)amino-5-hydroxymethyl]phenylcarbamate;
i-propyl N-[3-(4-chloroacridin-9-yl)amino-5-hydroxymethyl]phenylcarbamate;
n-butyl N-[3-(4-chloroacridin-9-yl)amino-5-hydroxymethyl]phenylcarbamate;
i-butyl N-[3-(4-chloroacridin-9-yl)amino-5-hydroxymethyl]phenylcarbamate;
t-butyl -N-[3-(4-chloroacridin-9-yl)amino-5-hydroxymethyl]phenylcarbamate;
phenyl N-[3-(4-chloroacridin-9-yl)amino-5-hydroxymethyl]phenylcarbamate;
methyl N-[3-(4-aminocarbonyl-5-methylacridin-9-yl) amino-5-hydroxymethyl]phenylcarbamate;
ethyl N-[3-(4-aminocarbonyl-5-methylacridin-9-yl)amino-5-hydroxymethyl]phenylcarbamate;
n-propyl N-[3-(4-aminocarbonyl-5-methylacridin-9-yl) amino-5-hydroxymethyl]phenylcarbamate;
i-propyl N-[3-(4-aminocarbonyl-5-methylacridin-9-yl) amino-5-hydroxymethyl]phenylcarbamate;
n-butyl N-[3-(4-aminocarbonyl-5-methylacridin-9-yl) amino-5-hydroxymethyl]phenylcarbamate;
i-butyl N-[3-(4-aminocarbonyl-5-methylacridin-9-yl) amino-5-hydroxymethyl]phenylcarbamate;
t-butyl N-[3-(4-aminocarbonyl-5-methylacridin-9-yl) amino-5-hydroxymethyl]phenylcarbamate;
phenyl N-[3-(4-aminocarbonyl-5-methylacridin-9-yl) amino-5-hydroxymethyl]phenylcarbamate;
methyl N-[3-(4-methylaminocarbonyl-5-methylacridin-9-yl)amino-5-hydroxymethyl]phenylcarbamate;
ethyl N-[3-(4-methylaminocarbonyl-5-methylacridin-9-yl) amino-5-hydroxymethyl]phenylcarbamate;
n-propyl N-[3-(4-methylaminocarbonyl-5-methylacridin-9-yl)amino-5-hydroxymethyl]phenylcarbamate;
i-propyl N-(3-(4-methylaminocarbonyl-5-methylacridin-9-yl)amino-5-hydroxymethyl]phenylcarbamate;
n-butyl N-[3-(4-methylaminocarbonyl-5-methylacridin-9-yl)amino-5-hydroxymethyl]phenylcarbamate;
i-butyl N-[3-(4-methylaminocarbonyl-5-methylacridin-9-yl)amino-5-hydroxymethyl]phenylcarbamate;
t-butyl N-[3-(4-methylaminocarbonyl-5-methylacridin-9-yl)amino-5-hydroxymethyl]phenylcarbamate;
phenyl N-[3-(4-methylaminocarbonyl-5-methylacridin-9-yl)amino-5-hydroxymethyl]phenylcarbamate;
methyl N-[3-(4-N,N-dimethylaminocarbonyl-5-methylacridin-9-yl)amino-5-hydroxymethyl] phenylcarbamate;
ethyl N-[3-(4-N,N-dimethylaminocarbonyl-5-methylacridin-9-yl)amino-5-hydroxymethyl] phenylcarbamate;
n-propyl N-[3-(4-N,N-dimethylaminocarbonyl-5-methylacridin-9-yl)amino-5-hydroxymethyl] phenylcarbamate;

i-propyl N-[3-(4-N,N-dimethylaminocarbonyl-5-methylacridin-9-yl)amino-5-hydroxymethyl]phenylcarbamate;

n-butyl N-[3-(4-N,N-dimethylaminocarbonyl-5-methylacridin-9-yl)amino-5-hydroxymethyl]-phenylcarbamate;

i-butyl N-[3[(4-N,N-dimethylaminocarbonyl-5-methylacridin-9-yl)amino-5-hydroxymethyl]-phenylcarbamate;

t-butyl N-[3-(4-N,N-dimethylaminocarbonyl-5-methylacridin-9-yl)amino-5-hydroxymethyl]phenylcarbamate;

phenyl N-[3-(4-N,N-dimethylaminocarbonyl-5-methylacridin-9-yl)amino-5-hydroxymethyl]phenylcarbamate;

methyl N-[3-(4-aminocarbonyl-5-methoxyacridin-9-yl)amino-5-hydroxymethyl]phenylcarbamate;

ethyl N-[3-(4-aminocarbonyl-5-methoxyacridin-9-yl)amino-5-hydroxymethyl]phenylcarbamate;

n-propyl N-[3-(4-aminocarbonyl-5-methoxyacridin-9-yl)amino-5-hydroxymethyl]phenylcarbamate;

i-propyl N-[3-(4-aminocarbonyl-5-methoxyacridin-9-yl)amino-5-hydroxymethyl]phenylcarbamate;

n-butyl N-[3-(4-aminocarbonyl-5-methoxyacridin-9-yl)amino-5-hydroxymethyl]phenylcarbamate;

i-butyl N-[3-(4-aminocarbonyl-5-methoxyacridin-9-yl)amino-5-hydroxymethyl]phenylcarbamate;

t-butyl N-[3-(4-aminocarbonyl-5-methoxyacridin-9-yl)amino-5-hydroxymethyl]phenylcarbamate;

phenyl N-[3-(4-aminocarbonyl-5-methoxyacridin-9-yl)amino-5-hydroxymethyl]phenylcarbamate;

methyl N-[3-(4-methylaminocarbonyl-5-methoxyacridin-9-yl)amino-5-hydroxymethyl]phenylcarbamate;

ethyl N-[3-(4-methylaminocarbonyl-5-methoxyacridin-9-yl)amino-5-hydroxymethyl]phenylcarbamate;

n-propyl N-[3-(4-methylaminocarbonyl-5-methoxyacridin-9-yl)amino-5-hydroxymethyl]phenylcarbamate;

i-propyl N-[3-(4-methylaminocarbonyl-5-methoxyacridin-9-yl)amino-5-hydroxymethyl]phenylcarbamate;

n-butyl N-[3-(4-methylaminocarbonyl-5-methoxyacridin-9-yl)amino-5-hydroxymethyl]phenylcarbamate;

i-butyl N-[3-(4-methylaminocarbonyl-5-methoxyacridin-9-yl)amino-5-hydroxymethyl]phenylcarbamate;

t-butyl N-[3-(4-methylaminocarbonyl-5-methoxyacridin-9-yl)amino-5-hydroxymethyl]phenylcarbamate;

phenyl N-[3-(4-methylaminocarbonyl-5-methoxyacridin-9-yl)amino-5-hydroxymethyl]phenylcarbamate;

methyl N-[3-(4-N,N-dimethylaminocarbonyl-5-methoxyacridin-9-yl)amino-5-hydroxymethyl]phenylcarbamate;

ethyl N-[3-(4-N,N-dimethylaminocarbonyl-5-methoxyacridin-9-yl)amino-5-hydroxymethyl]phenylcarbamate;

n-propyl N-[3-(4-N,N-dimethylaminocarbonyl-5-methoxyacridin-9-yl)amino-5-hydroxy-methyl]phenylcarbamate;

i-propyl N-[3-(4-N,N-dimethylaminocarbonyl-5-methoxyacridin-9-yl)amino-5-hydroxy-methyl]phenylcarbamate;

n-butyl N-[3-(4-N,N-dimethylaminocarbonyl-5-methoxylacridin-9-yl)amino-5-hydroxy-methyl]phenylcarbamate;

i-butyl N-[3-(4-N,N-dimethylaminocarbonyl-5-methoxyacridin-9-yl)amino-5-hydroxymethyl]phenylcarbamate;

t-butyl N-[3-(4-N,N-dimethylaminocarbonyl-5-methoxyacridin-9-yl)amino-5-hydroxymethyl]phenylcarbamate;

phenyl N-[3-(4-N,N-dimethylaminocarbonyl-5-methoxyacridin-9-yl)amino-5-hydroxymethyl]phenylcarbamate;

methyl N-[3-(acridin-9-yl)amino-5-acetyloxymethyl]phenylcarbamate;

ethyl N-[3-(acridin-9-yl)amino-5-acetyloxymethyl]phenylcarbamate;

n-propyl N-[3-(acridin-9-yl)amino-5-acetyloxymethyl]phenylcarbamate;

i-propyl N-[3-(acridin-9-yl)amino-5-acetyloxymethyl]phenylcarbamate;

n-butyl N-[3-(acridin-9-yl)amino-5-acetyloxymethyl]phenylcarbamate;

i-butyl N-[3-(acridin-9-yl)amino-5-acetyloxymethyl]phenylcarbamate;

t-butyl N-[3-(acridin-9-yl)amino-5-acetyloxymethyl]phenylcarbamate;

phenyl N-[3-(acridin-9-yl)amino-5-acetyloxymethyl]phenylcarbamate;

methyl N-[3-(acridin-9-yl)amino]-5-acetyloxymethyl]phenylcarbamate;

ethyl N-[3-[(acridin-9-yl)amino]-5-acetyloxymethyl]phenylcarbamate;

methyl N-[3-(4-methylaminocarbonylacridin-9-yl)amino-5-acetyloxymethyl]phenylcarbamate;

ethyl N-[3-(4-methylaminocarbonylacridin-9-yl)amino-5-acetyloxymethyl]phenylcarbamate;

methyl N-[3-(4-methylaminocarbonyl-5-methylacridin-9-yl)amino-5-acetyloxymethyl]phenylcarbamate;

ethyl N-[3-(4-methylaminocarbonyl-5-methylacridin-9-yl)amino-5-acetyloxymethyl]phenylcarbamate;

methyl N-[3-(4-methylaminocarbonyl-5-methoxyacridin-9-yl)amino-5-acetyloxymethyl]phenylcarbamate;

ethyl N-[3-(4-methylaminocarbonyl-5-methoxyacridin-9-yl)amino-5-acetyloxymethyl]phenylcarbamate;

methyl N-[3-(4-methylaminocarbonyl-6-nitroacridin-9-yl)amino-5-hydroxymethyl]phenylcarbamate;

ethyl N-[3-(4-methylaminocarbonyl-6-nitroacridin-9-yl)amino-5-hydroxymethyl]phenylcarbamate;

methyl N-[3-(4-methylaminocarbonyl-7-nitroacridin-9-yl)amino-5-hydroxymethyl]phenylcarbamate;

ethyl N-[3-(4-methylaminocarbonyl-7-nitroacridin-9-yl)amino-5-hydroxymethyl]phenylcarbamate;

methyl N-[3-(6-amino-4-methylaminocarbonylacridin-9-yl)amino-5-hydroxymethyl]phenylcarbamate;

ethyl N-[3-(6-amino-4-methylaminocarbonylacridin-9-yl)amino-5-hydroxymethyl]phenylcarbamate;

methyl N-[3-(7-amino-4-methylaminocarbonylacridin-9-yl)amino-5-hydroxymethyl]phenylcarbamate;

ethyl N-[3-(7-amino-4-methylaminocarbonylacridin-9-yl)amino-5-hydroxymethyl]phenylcarbamate;

methyl N-[3-(4-methylaminocarbonyl-6-methylaminoacridin-9-yl)amino-5-hydroxymethyl]phenylcarbamate;

ethyl N-[3-(4-methylaminocarbonyl-6-methylaminoacridin-9-yl)amino-5-hydroxymethyl]phenylcarbamate;

methyl N-[3-(4-methylaminocarbonyl-7-methylaminoacridin-9-yl)amino-5-hydroxymethyl]phenylcarbamate;

ethyl N-[3-(4-methylaminocarbonyl-7-methylaminoacridin-9-yl)amino-5-hydroxymethyl]phenylcarbamate;

methyl N-[3-(3,6-dinitroacridin-9-yl)amino-5-hydroxymethyl]phenylcarbamate;

ethyl N-[3-(3,6-dinitroacridin-9-yl)amino-5-hydroxymethyl]phenylcarbamate;

methyl N-[3-(4,5-dinitroacridin-9-yl)amino-5-hydroxymethyl]phenylcarbamate;

ethyl N-[3-(4,5-dinitroacridin-9-yl)amino-5-hydroxymethyl]phenylcarbamate;
methyl N-[3-(3,6-diaminoacridin-9-yl)amino-5-hydroxymethyl]phenylcarbamate;
ethyl N-[3-(3,6-diaminoacridin-9-yl)amino-5-hydroxymethyl]phenylcarbamate;
methyl N-{3-[3,6-bis(methylamino)acridin-9-yl]amino-5-hydroxymethyl}phenylcarbamate;
ethyl N-{3-[3,6-bis(methylamino)acridin-9-yl]amino-5-hydroxymethyl}phenylcarbamate;
methyl N-{3-[4,5-bis(methylamino)acridin-9-yl]amino-5-hydroxymethyl}phenylcarbamate;
ethyl N-{3-[4,5-bis(methylamino)acridin-9-yl]amino-5-hydroxymethyl}phenylcarbamate;
methyl N-{3-[3,6-bis(dimethylamino)acridin-9-yl]amino-5-hydroxymethyl}phenylcarbamate;
ethyl N-{3-[3,6-bis(dimethylamino)acridin-9-yl]amino-5-hydroxymethyl}phenylcarbamate;
methyl N-{3-[4,5-bis(dimethylamino)acridin-9-yl]amino-5-hydroxymethyl}phenylcarbamate;
ethyl N-{3-[4,5-bis(dimethylamino)acridin-9-yl]amino-5-hydroxymethyl}phenylcarbamate;
methyl N-{3-[3,6-bis(dimethylaminoethylamino)acridin-9-yl]amino-5-hydroxymethyl}phenylcarbamate;
ethyl N-{3-[3,6-bis(dimethylaminoethylamino)acridin-9-yl]amino-5-hydroxymethyl}phenylcarbamate;
methyl N-{3-[4,5-bis(dimethylaminoethylamino)acridin-9-yl]amino-5-hydroxymethyl}phenylcarbamate; and
ethyl N-{3-[4,5-bis(dimethylaminoethylamino)acridin-9-yl]amino-5-hydroxymethyl}phenylcarbamate.

The preferred compounds of Formula (I) are those wherein $R^2$, $R^3$ and $R^4$ are all hydrogen.

In the most preferred embodiment, $R^1$ is ethyl, $R^2$, $R^3$ and $R^4$ are hydrogen.

In the second aspect, the present invention provides a process for synthesizing the compounds of Formula (I) which comprises:

(a) condensing mono-, di- or multi-substituted 9-chloroacridines with 3,5-diaminobenzyl alcohol dihydrochloride under suitable conditions to form mono-, di-, or multi-substituted 3-(acridin-9-yl)amino-5-hydroxymethylanilines of Formula (II):

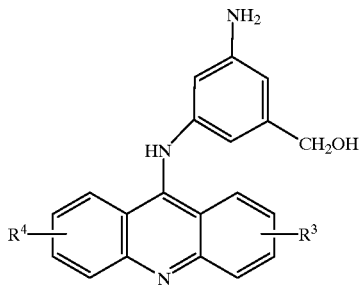

Formula (II)

wherein $R^3$ and $R^4$ are as defined above;

(b) treating the compounds of Formula (II) with a haloformate of the formula $XCOOR^i$ wherein X is a halogen and $R^i$ is $C_{1-6}$ alkyl or optionally substituted phenyl under suitable conditions to form the compounds of Formula (I) wherein $R^2$ is hydrogen;

(c) if desired, O-acylating the compounds of Formula (I) wherein $R^2$ is hydrogen under suitable conditions to form the compounds of Formula (I) wherein $R^2$ is an acyl group of the formula —$COR^a$ wherein $R^a$ is $C_{1-6}$ alkyl or phenyl; or $R^2$ is an acetylalkylcarbonyl group of the formula —$CO(CH_2)_nCOCH_3$ wherein n=1–3; and (d) if desired, converting the compounds of Formula (I) into the pharmaceutically salts thereof as appropriate.

In the preferred embodiment, the reaction in step (a) is performed in the presence of a base such as sodium carbonate, potassium carbonate, sodium hydroxide, potassium hydroxide, sodium hydride, potassium hydride, potassium t-butoxide, 4-methylmorpholine, triethylamine, N,N-dimethylaniline, N,N-diethylaniline, 4-(N,N-diethylamino) pyridine, 1,8-diazabicyclo[5.5.0]-undec-7ene (DBU), 1,4-diazabicyclo[2.2.2]octane (TED), 1,5-diazabicyclo[4.3.0]non-5-ene (DBN), 2,6-di-tert-butylpyridine, 2,6-di-tert-butyl-4-methylpyridine and other organic bases, in a solvent such as chloroform, dichloromethane, ethylene dichloride, carbon tetrachloride, ethylene tetrachloride, or ethers such as diethyl ether, tetrahydrofuran, dioxane or 2-methoxyethyl ether, or alcohol such as methanol, ethanol, propanol, 2-methoxyethanol or dimethylformamide, dimethylsulfoxide (DMSO) and the like. Preferably, the contacting is carried out in a mixture of 4-methyl-morpholine in chloroform and methanol and the like, at 0° C. to room temperature for a period of 0.5 hour to 2 days.

The molar ratio of the reactants in step (a) 9-chloroacridine to 3,5-diaminobenzyl alcohol dihydrochloride to 4-methylmorpholine can be 1 to 2 to 5, preferably 1.1 to 1 to 3.

Upon completion of the reaction in step (a), the precipitated product, for example, 3-(4-methylaminocarbonyl-5-methylacridin-9-yl)amino-5-hydroxymethylaniline, is collected by filtration. The reaction mixture can also be concentrated in vacuo, the residue is diluted with ice-water and the precipitated product is collected by filtration. The product is purified by either recrystallization or chromatography.

The treating in step (b) comprises the contacting of the compounds of Formula II with alkyl or phenyl haloformates to form the N-carbamates of Formula (I) wherein $R^2$ is hydrogen.

In one embodiment, the treating in step (b) comprises contacting the compounds formed in step (a) with a haloformate of the formula $XCOOR^i$ wherein X is halogen such as fluoro, chloro, bromo and iodo; and $R^i$ is $C_{1-6}$ alkyl or a optionally substituted phenyl group, such as methyl chloroformate, ethyl chloroformate, n-propyl chloroformate, i-propyl chloroformate, t-butyl chloroformate, phenyl chloroformate and the like to form alkyl or phenyl carbamates of Formula (I) wherein $R^2$ is hydrogen. In the preferred embodiment, the contacting is performed in the presence of base such as sodium carbonate, potassium carbonate, sodium hydroxide, potassium hydroxide, sodium hydride, potassium hydride, pyridine, 4-methylmorpholine, triethylamine, N,N-dimethylaniline, N,N-diethylaniline, 4-(N,N-diethylamino)pyridine, 1,8-diazabicyclo[5.5.0]-undec-7-ene (DBU), 1,4-diazabicyclo[2.2.2]octane (TED), 1,5-diazabicyclo[4.3.0]non-5-ene (DBN), 2,6-di-tert-butylpyridine, 2,6-di-tert-butyl-4-methylpyridine and other organic bases, in a solvent such as chloroform, dichloromethane, ethylene dichloride, carbon tetrachloride, ethylene tetrachloride, or ethers such as diethyl ether, tetrahydrofuran, dioxane or 2-methoxyethyl ether, or dimethylformamide (DMF), dimethyl-sulfoxide (DMSO) and the like at a temperature rang of from −10 to 50° C. for a period of 5 min to 2 days. The solvent is an alcohol, such as methanol, ethanol, propanol, or dimethylformamide, dimethylsulfoxide (DMSO) and the like. Preferably, the contacting is carried out in dimethylformamide (DMF) in the presence of pyridine at 0° C. for 15 min.

The molar ratio of the reactants in step (b) of 9-anilinoacridine derivatives to alkyl or phenyl haloformate to base (i.e. pyridine) can be 1 to 4 to 6, preferably 1 to 1.5 to 2.

Upon the completion of the reaction in step (b), the reaction mixture is evaporated to dryness in vacuo. The product is isolated and purified by recrystallization or chromatography.

The treating in step (c) comprises the O-acylation of the compounds of Formula (I) wherein $R^2$ is hydrogen to give the compounds of Formula (I) wherein $R^2$ is an acyl group of the formula —$COR^a$ wherein $R^a$ is $C_{1-6}$ alkyl or phenyl; or an acetylalkylcarbonyl group of the formula —$CO(CH_2)_nCOCH_3$ wherein n=1–3.

In the preferred embodiment, the O-acylated compound of Formula (I) is synthesized by treatment of alkyl carbamate derivatives of Formula (I) wherein $R^2$ is hydrogen formed in step (b) with an acid anhydride such as acetic anhydride, acetoacetic anhydride, levulinic acid anhydride, glutaric acid anhydride, succinic acid anhydride and the like, in the presence of 1,3-dicyclohexylcarbodiimde (DCC), metal alkoxide such as sodium methoxide, sodium ethoxide, potassium t-butoxide and the like, and an organic base such as triethylamine, N,N-diethylaniline, 4-dimethylaminopyridine and the like in a solvent at a temperature of from –5 to 100° C. for a period of one hour to 4 days. The solvent is pyridine, dimethylforamide and dimethylsulfoxide, diglyme and the like. Preferably, the reaction is carried out by treatment with 4-dimethylaminopyridine in the presence of DDC in pyridine at room temperature for 2 days.

In the preferred embodiment, the O-acylated compound of Formula (I) is synthesized by treatment with acyl chloride, acetyl chloride, acetoacetyl chloride, levulinyl chloride, acetylbutyryl chloride and the like in a solvent in the presence of acid or base at a temperature range of from 0 to 150° C. for a period of 20 min to 2 days. The acid is acetic acid, hydrogen chloride, hydrogen bromide, p-toluenesulfonic acid and the like. The base is metal alkoxide such as sodium methoxide, sodium ethoxide, potassium t-butoxide and the like, and an organic base such as triethylamine, N,N-diethylaniline, 4-dimethylaminopyridine. The solvent is acetic acid, benzene, toluene, dioxane, diglyme, dimethylformamide, dimethylsulfoxide and the like.

Upon completion of the reaction, the mixture is poured into water, neutralized with diluted acid such as acetic acid, hydrochloric acid, sulfuric acid and the like. The precipitated product is collected by filtration, followed by purification by either recrystallization or chromatography. If no precipitated product appears after neutralization, the mixture is extracted with organic solvent such as chloroform, methylene chloride or ethyl acetate and the like. The product is obtained by crystallization or chromatography.

Most of the intermediates of Formula (II) formed in step (b) are novel compounds. Accordingly, in another aspect, the present invention provides novel compounds of Formula (II)

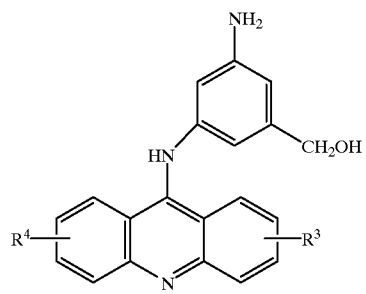

Formula (II)

wherein $R^3$ and $R^4$ are as defined above;
with the proviso that at least one of $R^3$ and $R^4$ is not hydrogen;
and the pharmaceutically acceptable salts thereof.

For illustrative purpose, the novel compounds of Formula (II) according to the invention can be selected from, but not limited to, the group consisting of the following:
3-(4-methylacridin-9-yl)amino-5-hydroxymethylaniline;
3-(4-nitroacridin-9-yl)amino-5-hydroxymethylaniline;
3-(4-methylaminoacridin-9-yl)amino-5-hydroxymethylaniline;
3-(4-N,N-dimethylaminoacridin-9-yl)amino-5-hydroxymethylaniline;
3-(4-methoxycarbonylacridin-9-yl)amino-5-hydroxymethylaniline;
3-(4-methylaminocarbonylacridin-9-yl)amino-5-hydroxymethylaniline;
3-(4-N,N-dimethylaminocarbonylacridin-9-yl)amino-5-hydroxymethylaniline;
3-(4-methoxyacridin-9-yl)amino-5-hydroxymethylaniline;
3-(4-N,N-dimethylaminocarbonyl-5-methoxyacridin-9-yl)amino-5-hydroxymethylaniline;
3-(acridin-9-yl)amino-5-acetyloxymethylaniline;
3-(4-methylaminocarbonylacridin-9-yl)amino-5-acetyloxymethylaniline;
3-(4-methylaminocarbonyl-5-methylacridin-9-yl)amino-5-acetyloxymethylaniline; and
3-(4-methylaminocarbonyl-5-methoxyacridin-9-yl)amino-5-acetyloxymethylaniline.

Based on Tables 1 and 2 infra, the compounds of Formula (I) are pharmacologically active. In view of the structural similarity, the compounds of Formula (II) as defined above are also pharmaceutically active.

Accordingly, the present invention further provides a pharmaceutical composition which comprises as the active ingredient an effective amount of the compound of Formula (I):

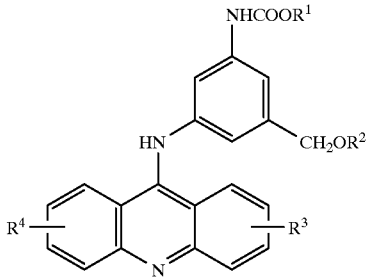

Formula (I)

wherein
R$^1$ is C$_{1-6}$ alkyl; or phenyl;
R$^2$ is hydrogen;
   an acyl group of the formula —COR$^a$ wherein R$^a$ is C$_{1-6}$ alkyl or phenyl; or
   an acetylalkylcarbonyl group of the formula —CO(CH$_2$)$_n$COCH$_3$ wherein n=1–3; and
R$^3$ and R$^4$ are substituents at different position(s) of the acridine ring (i.e. C-1'–C-8'), and R$^3$ and R$^4$ may be the same or different and independently represent:
hydrogen;
C$_{1-6}$ alkyl;
C$_{1-6}$ alkyloxy;
a nitro group;
an amino group of the formula —NR$^b$R$^c$ wherein R$^b$ and R$^c$ may be the same or different and independently represent hydrogen or C$_{1-6}$ alkyl;
an aminoalkylamino group of the formula —NH(CH$_2$)$_n$NR$^d$R$^e$ wherein R$^d$ and R$^e$ may be the same or different and independently represent hydrogen, C$_{1-6}$ alkyl, a hydroxyalkyl group of the formula —(CH$_2$)$_n$OH wherein n=1–3, or C$_{1-6}$ haloalkyl;
an alkylaminocarbonyl group of the formula —CONHR$^f$ wherein R$^f$ is C$_{1-6}$ alkyl;
an alkylaminoalkylaminocarbonyl group of the formula —CONH(CH$_2$)$_n$NR$^g$R$^h$ wherein n=1–5, and R$^g$ and R$^h$ may be the same or different and independently represent hydrogen, C$_{1-6}$ alkyl, or a nitro group;
a halogen group;
a hydroxyalkyl group of the formula —(CH$_2$)$_n$OH wherein n=1–3;
a carbamate group of the formula —CH$_2$CONHR$^f$ wherein R$^f$ is as defined above;
an alkylcarbonyloxymethyl group of the formula —CH$_2$OCOR$^f$ wherein R$^f$ is as defined above;
an alkyl sulfonate of the formula —SO$_3$R$^f$ wherein R$^f$ is as defined above; and
an alkylsulfonyl group of the formula —SO$_2$R$^f$ wherein R$^f$ is as defined above;
and the pharmaceutically acceptable salts thereof; in combination with the pharmaceutically acceptable carrier thereof.

Furthermore, the invention also provides a pharmaceutical composition which comprises as the active ingredient an effective amount of the compound of Formula (II)

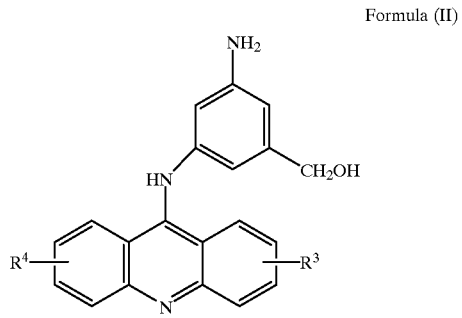

Formula (II)

wherein R$^3$ and R$^4$ are as defined above;
   with the proviso that at least one of R$^3$ and R$^4$ is not hydrogen;
and the pharmaceutically acceptable salts thereof; in combination with a pharmaceutically acceptable carrier thereof.

The present invention also provides the use of the compounds of Formula (I) and the novel compounds of Formula (II) for treating diseases. In particular, the invention provides the use of the above compounds for inhibiting growth of tumor cells.

The invention also provides methods of treating diseases. In particular, the invention provides methods of inhibiting growth of tumor cells which comprises contacting the tumor cells with an effective amount of the compounds of Formula (I) or the novel compounds of Formula (II).

The terms "an effective amount" used herein refer to the amount of compound enough to effectively exert an expected pharmaceutical effect. In particular, the effect is to inhibit growth of tumor cells. Preferably, the dose ranges from 1 to 500 mg/kg. Preferably, the compound has the structure of Formula I wherein R$^1$ is ethyl, R$^2$ R$^3$ and R$^4$ are hydrogen; R$^1$ is ethyl, R$^2$ is hydrogen, R$^3$ (C4') is CONHCH$_3$, and R$^4$ (C5') is CH$_3$.

The term "pharmaceutically acceptable carrier" used herein encompasses any of the standard pharmaceutical carriers such as sterile solutions, tablets, coated tablets, and capsules. Typically, such carriers contain excipients such as starch, milk, sugar, certain types of clay, gelatin, stearic acid, talc, vegetable fats or oils, gums, glycols, or other known excipients. Such carriers may also include flavor and color additives or other ingredients, such as compositions to increase solubility. Compositions which increase solubility include, but are not limit to, compounds which react with the hydrophobic regions of the subject compounds. Specifically, some examples of suitable agents include Emulphor (a polyoxyethylated fatty acid which is water miscible and non-toxic when diluted 1:10 with either sterile water or sterile physiological saline solution) and polyvinylpyrrolidone. Compositions comprising such carriers are formulated by well known conventional methods.

The pharmaceutical compositions of the invention can be administered via various routes, including but not limited to oral, intravenous, intramuscular and subcutaneous routes. The dosage form, administration routes, amount and frequency of delivery are expected to vary according to the situation, and will depend on which carrier is used, and what result is desired. However, those variables are readily determinable by one skilled in the art.

The following examples are set forth to aid in an understanding of the invention. These examples are not intended to, and should not be construed to, limit in any way the invention set forth in the claims which follow thereafter.

EXAMPLE 1

A mixture of known compound, 5-methylacridin-9-one 4-carboxylic acid (3.04 g, 12 mmol) (prepared in accordance with Denny et al., *J. Med. Chem.* 1987, 30:658 supra) and thionyl chloride (20 mL) containing 2 drops of dimethylformamide was gently refluxed for 40 min. The mixture was concentrated to a small volume, diluted with toluene and evaporated to dryness. The residue was dissolved in methylene chloride (200 mL), poured into excess of aqueous methylamine solution (40%, 20 mL) and vigorously stirred for 10 min. The organic layer was separated, washed with water (30 mL×3), dried (Na$_2$SO$_4$), and evaporated to dryness to give 9-chloro-5-methyl-4-methylaminocarbonylacridin-9-one (3.5 g), which was directly condensed with 3,5-diamino-5-hydroxymethylaniline dihydrochloride without further purification (see Example 2).

EXAMPLE 2

A suspension of 3,5-diaminobenzyl alcohol dihydrochloride (2.74 g, 13 mmol) in CHCl$_3$/EtOH (v/v, 1:3) was added dropwise 4-methylmorpholine (4.29 mL, 39 mmol) in an ice bath and stirred for 1 h. To this mixture a solution of above crude 9-chloro-5-methyl-4-methylamino-carbonylacridin-9-one (3.52 g, 13 mmol) (see Example 1) in CHCl$_3$ (15 mL) was added and stirred for additional 4 h. The solid product was collected by filtration. The filtered cake was washed well with CHCl$_3$ and recrystallized from MeOH to yield 3-(5-methyl-4-methylamino-carbonylacridin-9-yl)amino-5-hydroxymethylaniline, 3.90 g (78%), mp 275–278° C. (dec.).

$^1$H-NMR (DMSO-d$_6$): 2.83 (3H, s, CH$_3$), 3.11 (3H, s, NHCH$_3$) 4.54 (2H, s, CH$_2$), 5.50 (1H, br, exchangeable, OH), 6.65 (2H, br, NH$_2$), 6.64, 6.67, and 6.82 (each 1H, s, ArH), 7.52 and 7.67 (each 1H, t, ArH), 8.02, 8.26, 8.59 and 8.67 (each 1H, d, ArH), 9.78 and 11.92 (each 1H, br, NH). Analyses: Calculated for C$_{15}$H$_{11}$NO$_3$: C, 71.14; H, 4.38; N, 5.50. Found: C, 71.25; H, 4.22; N, 8.12.

By following the same procedure, the following acridine-ring substituted 3-(acridin-9-yl)amino-5-hydroxymethylaniline derivatives are synthesized:
3-(acridin-9-yl)amino-5-hydroxymethylaniline;
3-(4-methylacridin-9-yl)amino-5-hydroxymethylaniline;
3-(4-nitroacridin-9-yl)amino-5-hydroxymethylaniline;
3-(4-methylaminoacridin-9-yl)amino-5-hydroxymethylaniline;
3-(4-N,N-dimethylaminoacridin-9-yl)amino-5-hydroxymethylaniline;
3-(4-methoxycarbonylacridin-9-yl)amino-5-hydroxymethylaniline;
3-(4-methylaminocarbonylacridin-9-yl)amino-5-hydroxymethylaniline;
3-(4-N,N-dimethylaminocarbonylacridin-9-yl)amino-5-hydroxymethylaniline;
3-(4-methoxyacridin-9-yl)amino-5-hydroxymethylaniline;
3-(4-N,N-dimethylaminocarbonyl-5-methoxyacridin-9-yl)amino]-5-hydroxymethylaniline;
3-(acridin-9-yl)amino-5-acetyloxymethylaniline;
3-(4-methylaminocarbonylacridin-9-yl)amino-5-acetyloxymethylaniline;
3-(4-methylaminocarbonyl-5-methylacridin-9-yl)amino-5-acetyloxymethylaniline; and
3-(4-methylaminocarbonyl-5-methoxyacridin-9-yl)amino-5-acetyloxymethylaniline.

EXAMPLE 3

To a solution of 3-(acridin-9-yl)amino-5-hydroxymethylaniline (6.30 g, 20 mmol) in 80 mL of dimethylformamide (DMF) containing pyridine (3.2 mL, 40 mmol) was added dropwise ethyl chloroformate (3.24 g, 30 mmol) in an ice-bath. The mixture was stirred for 15 min and then evaporated in vacuo to dryness. The residue was chromatographed on a silica gel column (5×30 cm). The impurities were eluted with CHCl$_3$, and the product was then eluted by CHCl$_3$/MeOH(10:1, v/v). The fractions containing product were collected and concentrated, the residue was crystallized from EtOH to give ethyl N-[3-(acridin-9-yl)amino-5-hydroxy-methyl]phenylcarbamate, 6.32 g (82%), mp 226–228° C. (dec.). $^1$H-NMR (DMSO-d$_6$): 1.06 (H, s, J=7.0 Hz, CH$_3$), 4.10 (2H, q, J=7.0 Hz, CH$_2$), 4.45, (2H, s, CH$_2$), 5.35 (1H, br, OH), 6.97 (1H, s, ArH), 7.45–7.51 (4H, m, ArH), 8.01 (2H, m, ArH), 8.10 (2H, d, J=7.5 Hz), 8.27 (2H, d, J=8.79 Hz), 9.91 (1H, s, exchangeable, NH), 11.91 (1H, br, NH). Analyses: calculated for C$_{23}$H$_{21}$N$_3$O$_3$: C, 71.30; H, 5.46; N, 10.85. Found C, 71.42; H, 5.38; N, 10.69.

By following the same procedure, reaction of 3-(5-methyl-4-methylaminocarbonyl-acridin-9-yl)amino-5-hydroxymethylaniline (732 mg, 2 mmol) and ethyl chloroformate affords ethyl N-[3-(5-methyl-4-methylaminocarbonylacridin-9-yl]phenylcarbamate, 596 mg (65%), mp 252–253° C. (dec.). $^1$H-NMR (DMSO-d$_6$) : 1.43 (3H, t, J=7.2 Hz), 2.93 (3H, s, CH$_3$), 3.17 (3H, s, NHCH$_3$), 4.31 (2H, q, J=7.2 Hz, CH$_2$), 4.64 (2H, s, CH$_2$), 5.52 (1H, br, OH), 7.14 (1H, ArH), 7.55–7.78 (4H, m, ArH), 8.10, 8.33, 8.68 and 8.87 (each 1H, d, ArH), 9.80, 10.11 and 11.57 (each 1H, br, exchangeable, NH). Analyses: calculated for C$_{26}$H$_{26}$N$_4$O$_4$: C, 68.11; H, 5.72; N, 12.22. Found C, 68.23; H, 5.79; N, 12.14.

By following the same procedure, the following alkylcarbamate derivatives are synthesized:
ethyl N-[3-(acridin-9-yl)amino-5-hydroxymethyl]phenylcarbamate;
i-propyl N-[3-(acridin-9-yl)amino-5-hydroxymethyl]phenylcarbamate;
phenyl N-[3-(acridin-9-yl)amino-5-hydroxymethyl]phenylcarbamate;
ethyl N-[3-(4-methylacridin-9-yl)amino-5-hydroxymethyl]phenylcarbamate;
ethyl N-[3-(4-nitroacridin-9-yl)amino-5-hydroxymethyl]phenylcarbamate;
ethyl N-[3-(4-aminoacridin-9-yl)amino-5-hydroxymethyl]phenylcarbamate;
ethyl N-[3-(4-methylaminoacridin-9-yl)amino-5-hydroxymethyl]phenylcarbamate;
ethyl N-[3-(4-N,N-dimethylaminoacridin-9-yl)amino-5-hydroxymethyl]phenylcarbamate;
ethyl N-[3-(4-methoxycarbonylacridin-9-yl)amino-5-hydroxymethyl]phenylcarbamate;
ethyl N-[3-(4-methylaminocarbonylacridin-9-yl)amino-5-hydroxymethyl]phenylcarbamate;
ethyl N-[3-(4-N,N-dimethylaminocarbonylacridin-9-yl)amino-5-hydroxymethyl]phenylcarbamate;
ethyl N-[3-(4-methoxyacridin-9-yl)amino-5-hydroxymethyl]phenylcarbamate;
ethyl N-[3-(4-N,N-dimethylaminocarbonyl-5-methoxyacridin-9-yl)amino-5-hydroxymethyl]phenylcarbamate;
ethyl N-[3-(acridin-9-yl)amino-5-acetyloxymethyl]phenylcarbamate;
ethyl N-[3-(4-methylaminocarbonylacridin-9-yl)amino-5-acetyloxymethyl]phenylcarbamate;
ethyl N-[3-(4-methylaminocarbonyl-5-methylacridin-9-yl)amino-5-acetyloxymethyl]phenylcarbamate; and
ethyl N-[3-(4-methylaminocarbonyl-5-methoxyacridin-9-yl)amino-5-acetyloxymethyl]phenylcarbamate.

Pharmacological Experiments

The in vitro cytotoxicity of the N-[3-(acridin-9-yl)amino-5-hydroxymethyl]phenylcarbamate derivatives of the invention against growth of human leukemic HL-60 cells and 833K tumor cells, and the chemotherapeutic effects of ethyl N-[3-(acridin-9-yl)amino-5-hydroxymethyl]phenylcarbamate on Sarcoma 180 and Lewis lung carcinoma tumor bearing B$_6$D$_2$F$_1$ mice were evaluated. The compound 3-(acridin-9-yl)amino-5-hydroxymethylaniline (AHMA) was also evaluated for comparison. The results are shown in the following tables.

TABLE 1

The in vitro cytotoxicity against growth of human leukemic HL-60 cells and 833K tumor cells.

| Compd. | $R^1$ | $R^2$ | 4'-$R^3$ | 5'-$R^4$ | IC$_{50}$ for cell growth inhibition HL-60 ($\mu$M) | 833K |
|---|---|---|---|---|---|---|
| 1 (AHMA) | H | H | H | H | 0.025 | — |
| 2 | COOEt | H | H | H | 0.016 | 0.020 |
| 3 | COOCH$_2$CHMe$_2$ | H | H | H | 0.018 | 0.021 |
| 4 | H | H | H | CONHMe | Me | 0.144 | 0.244 |
| 5 | COOEt | H | CONHMe | Me | 0.083 | 0.034 |

TABLE 2

The chemotherapeutic effects on Sarcoma 180 and Lewis lung carcinoma tumor bearing B$_6$D$_2$F$_1$ mice.[a]

| Tumors | Dose (mg/kg) | Average Weight Change (gm) | | Average Tumor Volume (T/C) | |
|---|---|---|---|---|---|
| | | Day 7 | Day 10 | Day 7 | Day 10 |
| Sarcoma 180 | Control | −0.5 | +0.7 | 1.00 | 1.00 |
| | 3.0 | −2.0 | −0.7 | 1.24 | 1.21 |
| | 5.0 | −2.6 | +1.0 | 0.06 | 0.63 |
| | 7.0 | −3.4 | −0.1 | 0.22 | <0.01[b] |
| Lewis Lung Carcinoma | Control | −1 | −0.1 | 1 | 1 |
| | 3.0 | −2.3 | −1.3 | 0.8 | 0.63 |
| | 6.0 | −3 | −2.6 | 0.44 | 0.37 |
| | 8.0[c] | −3.6 | — | 0.21 | — |

[a]. Sarcoma 180 (3 × 10$^6$ cells) innoculated subcutaneously (s.c.) on day 0. Treatment started on day 1, peritoneal injection (i.p.), QD × 5. Control had 4 mice and each dose had 2 mice. Lewis lung carcinoma (4 × 20$^6$ cells) inoculated s.c. on day (−2). Treatment started on day 1, i.p., QD × 5. Control had 4 mice and each dose had 3 mice. Tumor sizes were evaluated on day 7 and day 10.
[b]. Tumor not detectable.
[c]. One mouse died on day 8 and two mice died on day 9.

As clearly shown, as AHMA possesses potent antitumor activity against growth of leukemia and several solid tumors both in vitro and in vivo with long half-life, the antitumor activity of the compounds according to the invention are found to be more potent than their precursors AHMA derivatives.

What is claimed is:

1. A compound of Formula (I)

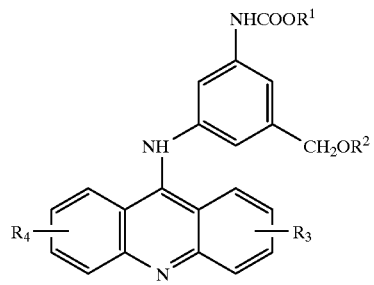

wherein
$R^1$ is C$_{1-6}$ alkyl; or phenyl;
$R^2$ is hydrogen;
an acyl group of the formula —COR$^a$ wherein R$^a$ is C$_{1-6}$ alkyl or phenyl; or
an acetylalkylcarbonyl group of the formula —CO(CH$_2$)$_n$COCH$_3$ wherein n=1–3; and $R^3$ and $R^4$ are substituents at different positions of the acridine ring (i.e. C-1'–C-8'), and $R^3$ and $R^4$ may be the same or different and independently represent:
hydrogen;
C$_{1-6}$ alkyl;
C$_{1-6}$ alkyloxy;
a nitro group;
an aminoalkylamino group of the formula —NH(CH$_2$)$_n$NR$^d$R$^e$ wherein R$^d$ and R$^e$ may be the same or different and independently represent hydrogen, C$_{1-6}$ alkyl, a hydroxyalkyl group of the formula —(CH$_2$)$_n$OH wherein n=1–3, or C$_{1-6}$ haloalkyl;
an alkylaminocarbonyl group of the formula —CONHR$^f$ wherein R$^f$ is C$_{1-6}$ alkyl;
an alkylaminoalkylaminocarbonyl group of the formula —CONH(CH$_2$)$_n$NR$^g$R$^h$ wherein n=1–5, and R$^g$ and R$^h$ may be the same or different and independently represent hydrogen, or C$_{1-6}$ alkyl;
a halogen group;
a carbamate group of the formula —CH$_2$CONHR$^f$ wherein R$^f$ is as defined above;
an alkylcarbonyloxymethyl group of the formula —CH$_2$OCOR$^f$ wherein R$^f$ is as defined above;
an alkyl sulfonate of the formula —SO$_3$R$^f$ wherein R$^f$ is as defined above; and
an alkylsulfonyl group of the formula —SO$_2$R$^f$ wherein R$^f$ is as defined above;
with the proviso that when R$^2$, R$^3$ and R$^4$ are hydrogen, R$^1$ is not t-butyl;
and the pharmaceutically acceptable salts thereof.

2. The compound of claim 1 selected from the group consisting of:
methyl N-[3-(acridin-9-yl)amino-5-hydroxymethyl]phenylcarbamate;
ethyl N-[3-(acridin-9-yl)amino-5-hydroxymethyl]phenylcarbamate;
n-propyl N-[3-(acridin-9-yl)amino-5-hydroxymethyl]-phenylcarbamate;
i-propyl N-[3-(acridin-9-yl)amino-5-liydroxymethyl]-phenylcarbamate;
i-butyl N-[3-(acridin-9-yl)amino-5-hydroxymethyl]-phenylcarbamate;
phenyl N-[3-(acridin-9-yl)amino-5-hydroxymethyl]-phenylcarbamate;
methyl N-[3-(3-methylacridin-9-yl)amino-5-hydroxymethyl]phenylcarbamate;
ethyl N-[3-(3-methylacridin-9-yl)amino-5-hydroxymethyl]-phenylcarbamate;
n-propyl N-[3-(3-methylacridin-9-yl)amino-5-hydroxymethyl]phenylcarbamate;
i-propyl N-[3-(3-methylacridin-9-yl)amino-5-hydroxymethyl]phenylcarbamate;
n-butyl N-[3-(3-methylacridin-9-yl)amino-5-hydroxymethyl]phenylcarbamate;
i-butyl N-[3-(3-methylacridin-9-yl)amino-5-hydroxymethyl]phenylcarbamate;
t-butyl N-[3-(3-methylacridin-9-yl)amino-5-hydroxymethyl]phenylcarbanate;
phenyl N-[3-(3-methylacridin-9-yl)amino-5-hydroxymethyl]phenylcarbamate;
methyl N-[3-(4--methylacridin-9-yl)amino-5-hydroxymethyl]phenylcarbamate;
ethyl N-[3-(4-methylacridin-9-yl)amino-5-hydroxymethyl]-phenylcarbamate;
n-propyl N-[3-(4-methylacridin-9-yl)amino-5-hydroxymethyl]phenylcarbanate;
i-propyl N-[3-(4-methylacridin-9-yl)amino-5-hydroxymethyl]phenylcarbamate;

n-butyl N-[3-(4-methylacridin-9-yl)amino-5-hydroxy-methyl]phenylcarbamate;
i-butyl N-[3-(4-methylacridin-9-yl)amino-5-hydroxy-methyl]phenylcarbamate;
t-butyl N-[3-(4-methylacidin-9-yl)amino-5-hydroxy-methyl]phenylcarbamate;
phenyl N-[3-(4-methylacridin-9-yl)amino-5-hydroxy-methyl]phenylcarbamate;
methyl N-[3-(3-nitroacridin-9-yl)amino-5-hydroxymethyl]-phenylcarbamate;
ethyl N-[3-(3-nitroacridin-9-yl)amino-5-hydroxymethyl]-phenylcarbamate;
n-propyl N-[3-(3-nitroacridin-9-yl)amino-5-hydroxy-methyl]phenylcarbamate;
i-propyl N-[3-(3-nitroacridin-9-yl)amino-5-hydroxy-methyl]phenylcarbamate;
n-butyl N-[3-(3 -nitroacridin-9-yl)amino-5-hydroxy-methyl]phenylcarbamate;
i-butyl N-[3-(3-nitroacridin-9-yl)amino-5-hydroxy-methyl]phenylcarbamate;
t-butyl N-[3-(3-nitroacridin-9-yl)amino-5-hydroxy-methyl]phenylcarbamate;
phenyl N-[3-(3-nitroacridin-9-yl)amino-5-hydroxymethyl]-phenylcarbamate;
methyl N-[3-(4-nitroacridin-9-yl)amino-5-hydroxymethyl]-phenylcarbamate;
ethyl N-[3-(4-nitroacridin-9-yl)amino-5-hydroxymethyl]-phenylcarbamate;
n-propyl N-[3-(4-nitroacridin-9-yl)amino-5-hydroxy-methyl]phenylcarbamate;
i-propyl N-[3-(4-nitroacridin-9-yl)amino-5-hydroxy-methyl]phenylcarbamate;
n-butyl N-[3-(4-nitroacridin-9-yl)amino-5-hydroxy-methyl]phenylcarbamate;
i-butyl N-[3-(4-nitroacridin-9-yl)amino-5-hydroxy-methyl]phenylcarbamate;
t-butyl N-[3-(4-nitroacridin-9-yl)amino-5-hydroxy-methyl]phenylcarbamate;
phenyl N-[3-(4-nitroacridin-9-yl)amino-5-hydroxymethyl]-phenylcarbamate;
methyl N-[3-(3-hydroxycarbonylacridin-9-yl)amino-5-hydroxymethyl]phenylcarbamate;
ethyl N-[3-(3-hydroxycarbonylacridin-9-yl)amino-5-hydroxymethyl]phenylcarbamate;
n-propyl N-[3-(3-hydroxycarbonylacridin-9-yl)amino-5-hydroxymethyl]phenylcarbanate;
i-propyl N-[3-(3-hydroxycarbonylacridin-9-yl)amino-5-hydroxymethyl]phenylcarbamate;
n-butyl N-[3-(3-hydroxycarbonylacridin-9-yl)amino-5-hydroxymethyl]phenylcarbamate;
i-butyl N-[3-(3-hydroxycarbonylacridin-9-yl)amino-5-hydroxymethyl]phenylcarbamate;
t-butyl N-[3-(3-hydroxycarbonylacridin-9-yl)amino-5-hydroxymethyl]phenylcarbamate;
phenyl N-[3-(3-hydroxycarbonylacridin-9-yl)amino-5-hydroxymethyl]phenylcarbamate;
methyl N-[3-(4-hydroxycarbonylacridin-9-yl)amino-5-hydroxymethyl]phenylcarbamate;
ethyl N-[3-(4-hydroxycarbonylacridin-9-yl)amino-5-hydroxymethyl]phenylcarbamate;
n-propyl N-[3-(4-hydroxycarbonylacridin-9-yl)amino-5-hydroxymethyl]phenylcarbamate;
i-propyl N-[3-(4-hydroxycarbonylacridin-9-yl)amino-5-hydroxymethyl]phenylcarbamate;
n-butyl N-[3-(4-hydroxycarbonylacridin-9-yl)amino-5-hydroxymethyl]phenylcarbamate;
i-butyl N-[3-(4-hydroxycarbonylacridin-9-yl)amino-5-hydroxy-methyl]phenylcarbamate;
t-butyl N-[3-(4-hydroxycarbonylacridin-9-yl)amino-5-hydroxy-methyl]phenylcarbamate;
phenyl N-[3-(4-hydroxycarbonylacridin-9-yl)amino-5-hydroxymethyl]phenylcarbamate;
methyl N-[3-(3-methoxycarbonylacridin-9-yl)amino-5-hydroxymethyl]phenylcarbamate;
ethyl N-[3-(3-methoxycarbonylacridin-9-yl)amino-5-hydroxymethyl]phenylcarbamate;
n-propyl N-[3-(3-methoxycarbonylacridin-9-yl)amino-5-hydroxymethyl]phenylcarbamate;
i-propyl N-[3-(3-methoxycarbonylacridin-9-yl)amino-5-hydroxymethyl]phenylcarbamate;
n-butyl N-[3-(3-methoxycarbonylacridin-9-yl)amino-5-hydroxymethyl]phenylcarbamate;
i-butyl N-[3-(3-methoxycarbonylacridin-9-yl)amino-5-hydroxymethyl]phenylcarbamate;
t-butyl N-[3-(3-methoxycarbonylacridin-9-yl)amino-5-hydroxymethyl]phenylcarbamate;
phenyl N-[3-(3-methoxycarbonylacridin-9-yl)amino-5-hydroxymethyl]phenylcarbamate;
methyl N-[3-(4-methoxycarbonylacridin-9-yl)amino-5-hydroxymethyl]phenylcarbamate;
ethyl N-[3-(4-methoxycarbonylacridin-9-yl)amino-5-hydroxymethyl]phenylcarbamate;
n-propyl N-[3-(4-methoxycarbonylacridin-9-yl)amino-5-hydroxymethyl]phenylcarbamate;
i-propyl N-[3-(4-methoxycarbonylacridin-9-yl)amino-5-hydroxymethyl]phenylcarbamate;
n-butyl N-[3-(4-methoxycarbonylacridin-9-yl)amino-5-hydroxymethyl]phenylcarbamate;
i-butyl N-[3-(4-methoxycarbonylacridin-9-yl)amino-5-hydroxymethyl]phenylcarbamate;
t-butyl N-[3-(4-methoxycarbonylacridin-9-yl)amino-5-hydroxy-methyl]phenylcarbamate;
phenyl N-[3-(4-methoxycarbonylacridin-9-yl)amino-5-hydroxymethyl]phenylcarbamate;
methyl N-[3-(3-aminocarbonylacridin-9-yl)amino-5-hydroxymethyl]phenylcarbamate;
ethyl N-[3-(3-aminocarbonylacridin-9-yl)amino-5-hydroxymethyl]phenylcarbamate;
n-propyl N-[3-(3-aminocarbonylacridin-9-yl)amino-5-hydroxymethyl]phenylcarbamate;
i-propyl N-[3-(3-aminocarbonylacridin-9-yl)amino-5-hydroxymethyl]phenylcarbamate;
n-butyl N-[3-(3-aminocarbonylacridin-9-yl)amino-5-hydroxymethyl]phenylcarbamate;
i-butyl N-[3-(3-aminocarbonylacridin-9-yl)amino-5-hydroxymethyl]phenylcarbatnate;
t-butyl N-[3-(3-aminocarbonylacridin-9-yl)amino-5-hydroxymethyl]phenylcarbamate;
phenyl N-[3-(3-aminocarbonylacridin-9-yl)amino-5-hydroxymethyl]phenylcarbamate;
methyl N-[3-(4-aminocarbonylacridin-9-yl)amino-5-hydroxymethyl]phenylcarbamate;
ethyl N-[3-(4-aminocarbonylacridin-9-yl)amino-5-hydroxymethyl]phenylcarbamate;
n-propyl N-[3-(4-aminocarbonylacridin-9-yl)amino-5-hydroxymethyl]phenylcarbamate;
i-propyl N-[3-(4-aminocarbonylacridin-9-yl)amino-5-hydroxymethyl]phenylcarbamate;
n-butyl N-[3-(4-aminocarbonylacridin-9-yl)amino-5-hydroxymethyl]phenylcarbamate;
i-butyl N-[3-(4-aminocarbonylacridin-9-yl)amino-5-hydroxymethyl]phenylcarbamate;
t-butyl N-[3-(4-aminocarbonylacridin-9-yl)amino-5-hydroxymethyl]phenylcarbamate;
phenyl N-[3-(4-aminocarbonylacridin-9-yl)amino-5-hydroxymethyl]phenylcarbamate;

methyl N-[3-(3-methylaminocarbonylacridin-9-yl)amino-5-hydroxymethyl]phenylcarbamate;
ethyl N-[3-(3-methylaminocarbonylacridin-9-yl)amino-5-hydroxy-methyl]phenylcarbamate;
n-propyl N-[3-(3-methylaminocarbonylacridin-9-yl)amino-5-hydroxymethyl]phenylcarbamate;
i-propyl N-[3-(3-methylaminocarbonylacridin-9-yl)amino-5-hydroxymethyl]phenylcarbamate;
n-butyl N-[3-(3-methylaminocarbonylacridin-9-yl)amino-5-hydroxymethyl]phenylcarbamate;
i-butyl N-[3-(3-methylaminocarbonylacridin-9-yl)amino-5-hydroxymethyl]phenylcarbamate;
t-butyl N-[3-(3-methylaminocarbonylacridin-9-yl)amino-5-hydroxymethyl]phenylcarbamate;
phenyl N-[3-(3-methylaminocarbonylacridin-9-yl)amino-5-hydroxymethyl]phenylcarbamate;
methyl N-[3-(4-methylaminacarbonylacridin-9-yl)amino-5-hydroxymethyl]phenylcarbamate;
ethyl N-[3-(4-methylaminocarbonylacridin-9-yl)amino-5-hydroxymethyl]phenylcarbamate;
n-propyl N-[3-(4-methylaminocarbonylacridin-9-yl)amino-5-hydroxymethyl]phenylcarbamate;
i-propyl N-[3-(4-methylaminocarbonylacridin-9-yl)amino-5-hydroxymethyl]phenylcarbamate;
n-butyl N-[3-(4-methylaminocarbonylacridin-9-yl)amino-5-hydroxymethyl]phenylcarbamate;
i-butyl N-[3-(4-methylaminocarbonylacridin-9-yl)amino-5-hydroxymethyl]phenylcarbamate;
t-butyl N-[3-(4-methylaminocarbonylacridin-9-yl)amino-5-hydroxymethyl]phenylcarbamate;
phenyl N-[3-(4-methylaminocarbonylacridin-9-yl)amino-5-hydroxymethyl]phenylcarbamate;
methyl N-[3-(3-N,N-dimethylaminocarbonylacridin-9-yl)amino-5-hydroxymethyl]phenylcarbamate;
ethyl N-[3-(3-N,N-dimethylaminocarbonylacridin-9-yl)amino-5-hydroxymethyl]phenylcarbamate;
n-propyl N-[3-(3-N,N-dimethylaminocarbonylacridin-9-yl)amino-5-hydroxymethyl]phenylcarbamate;
i-propyl N-[3-(3-N,N-dimethylaminocarbonylacridin-9-yl)amino-5-hydroxymethyl]phenylcarbamate;
n-butyl N-[3-(3-N,N-dimethylaminocarbonylacridin-9-yl)amino-5-hydroxymethyl]phenylcarbamate;
i-butyl N-[3-(3-N,N-dimethylaminocarbonylacridin-9-yl)amino-5-hydroxymethyl]phenylcarbamate;
t-butyl N-[3-(3-N,N-dimethylaminocarbonylacridin-9-yl)amino-5-hydroxymethyl]phenylcarbamate;
phenyl N-[3-(3-N,N-dimethylaminocarbonylacridin-9-yl)amino-5-hydroxymethyl]phenylcarbamate;
methyl N-[3-(4-N,N-dimethylaminocarbonylacridin-9-yl)amino-5-hydroxymethyl]phenylcarbamate;
ethyl N-[3-(4-N,N-dimethylaminocarbonylacridin-9-yl)amino-5-hydroxymethyl]phenylcarbamate;
n-propyl N-[3-(4-N,N-dimethylaminocarbonylacridin-9-yl)amino-5-hydroxymethyl]phenylcarbamate;
i-propyl N-[3-(4-N,N-dimethylaminocarbonylacridin-9-yl)amino-5-hydroxymethyl]phenylcarbamate;
n-butyl N-[3-(4-N,N-dimethylaminocarbonylacridin-9-yl)amino-5-hydroxymethyl]phenylcarbamate;
i-butyl N-[3-(4-N,N-dimethylaminocarbonylacridin-9-yl)amino-5-hydroxymethyl]phenylcarbamate;
t-butyl N-[3-(4-N,N-dimethylaminocarbonylacridin-9-yl)amino-5-hydroxymethyl]phenylcarbamate;
phenyl N-[3-(4-N,N-dimethylaminocarbonylacridin-9-yl)amino-5-hydroxymethyl]phenylcarbamate;
methyl N-[3-(3methoxyacridin-9-yl)amino-5-hydroxymethyl]phenylcarbamate;
ethyl N-[3-(3-methoxyacridin-9-yl)amino-5-hydroxymethyl]phenylcarbamate;
n-propyl N-[3-(3-methoxyacridin-9-yl)amino-5-hydroxymethyl]phenylcarbamate;
i-propyl N-[3-(3-methoxyacridin-9-yl)amino-5-hydroxymethyl]phenylcarbamate;
n-butyl N-[3-(3-methoxyacridin-9-yl)amino-5-hydroxymethyl]phenylcarbamate;
i-butyl N-[3-(3-methoxyacridin-9-yl)amino-5-hydroxymethyl]phenylcarbamate;
t-butyl N-[3-(3-methoxyacridin-9-yl)amino-5-hydroxymethyl]phenylcarbamate;
phenyl N-[3-(3-methoxyacridin-9-yl)amino-5-hydroxymethyl]phenylcarbamate;
methyl N-[3-(4-methoxyacridin-9-yl)amino-5-hydroxymethyl]phenylcarbamate;
ethyl N-[3-(4-methoxyacridin-9-yl)amino-5-hydroxymethyl]phenylcarbamate;
n-propyl N-[3-(4-methoxyacridin-9-yl)amino-5-hydroxymethyl]phenylcarbamate;
i-propyl N-[3-(4-methoxyacridin-9-yl)amino-5-hydroxymethyl]phenylcarbamate;
n-butyl N-[3-(4-methoxyacridin-9-yl)amino-5-hydroxymethyl]phenylcarbamate;
i-butyl N-[3-(4-methoxyacridin-9-yl)amino-5-hydroxymethyl]phenylcarbanate;
t-butyl N-[3-(4-methoxyacridin-9-yl)amino-5-hydroxymethyl]phenylcarbamate;
phenyl N-[3-(4-methoxyacridin-9-yl)amino-5-hydroxymethyl]phenylcarbamate;
methyl N-[3-(3-chloroacridin-9-yl)amino-5-hydroxymethyl]phenylcarbamate;
ethyl N-[3-(3-chloroacridin-9-yl)amino-5-hydroxymethyl]phenylcarbamate;
n-propyl N-[3-(3-chloroacridin-9-yl)amino-5-hydroxymethyl]phenylcarbamate;
i-propyl N-[3-(3-chloroacridin-9-yl)amino-s-hydroxymethyl]phenylcarbamate;
n-butyl N-[3-(3-chloroacridin-9-yl)amino-5-hydroxymethyl]phenylcarbamate;
i-butyl N-[3-(3-chloroacridin-9-yl)amino-5-hydroxymethyl]phenylcarbamate;
t-butyl N-[3-(3-chloroacridin-9-yl)amino-5-hydroxymethyl]phenylcarbamate;
phenyl N-[3(3-chloroacridin-9-yl)amino-5-hydroxymethyl]phenylcarbamate;
methyl N-[3-(4-chloroacridin-9-yl)amino-5-hydroxymethyl]phenylcarbamate;
ethyl N-[3-(4-chloroacridin-9-yl)amino-5-hydroxymethyl]phenylcarbamate;
n-propyl N-[3-(4-chloroacridin-9-yl)amino-5-hydroxymethyl]phenylcarbamate;
i-propyl N-[3-(4-chloroacridin-9-yl)amino-5-hydroxymethyl]phenylcarbamate;
n-butyl N-[3-(4-chloroacridin-9-yl)amino-5-hydroxymethyl]phenylcarbamate;
i-butyl N-[3-(4-chloroacridin-9-yl)amino-5-hydroxymethyl]phenylcarbamate;
t-butyl —N-[3-(4-chloroacridin-9-yl)amino-5-hydroxymethyl]phenylcarbamate;
phenyl N-[3-(4-chloroacridin-9-yl)amino-5-hydroxymethyl]phenylcarbamate;
methyl N-[3-(4-aminocarbonyl-5-methylacridin-9-yl)amino-5-hydroxymethyl]phenylcarbamate;
ethyl N-[3-(4-aminocarbonyl-5-methylacridin-9-yl)amino-5-hydroxymethyl]phenylcarbamate;
n-propyl N-[3-(4-aminocarbonyl-5-methylacridin-9-yl)-amino-5-hydroxymethyl]phenylcarbamate;
i-propyl N-[3-(4-aminocarbonyl-5-methylacridin-9-yl)-amino-5-hydroxymethyl]phenylcarbamate;

n-butyl N-[3-(4-aminocarbonyl-5-methylacridin-9-yl)-amino-5-hydroxymethyl]phenylcarbamate;
i-butyl N-[3-(4-aminocarbonyl-5-methylacridin-9-yl)-amino-5-hydroxymethyl]phenylcarbamate;
t-butyl N-[3-(4-aminocarbonyl-5-methylacridin-9-yl)-amino-5-hydroxymethyl]phenylcarbamate;
phenyl N-[3-(4-aminocarbonyl-5-methylacridin-9-yl)amino-5-hydroxymethyl]phenylcarbamate;
methyl N-[3-(4-methylaminocarbonyl-5-methylacridin-9-yl)amino-5-hydroxymethyl]phenylcarbamate;
ethyl N-[3-(4-methylaminocarbonyl-5-methylacridin-9-yl)-amino-5-hydroxymethyl]phenylcarbamate;
n-propyl N-[3-(4-methylaminocarbonyl-5-methylacridin-9-yl)amino-5-hydroxymethyl]phenylcarbamate;
i-propyl N-[3-(4-methylaminocarbonyl-5-methylacridin-9-yl)amino-5-hydroxymethyl]phenylcarbamate;
n-butyl N-[3-(4-methylaminocarbonyl-5-methylacridin-9-yl)amino-5-hydroxymethyl]phenylcarbamate;
i-butyl N-[3-(4-methylaminocarbonyl-5-methylacridin-9-yl)amino-5-hydroxymethyl]phenylcarbamate;
t-butyl N-[3-(4-methylaminocarbonyl-5-methylacridin-9-yl)amino-5-hydroxymethyl]phenylcarbamate;
phenyl N-[3-(4-methylaminocarbonyl-5-methylacridin-9-yl)amino-5-hydroxymethyl]phenylcarbamate;
methyl N-[3-(4-N,N-dimethylaminocarbonyl-5-methyl-acridin-9-yl)amino-5-hydroxymethyl]phenylcarbamate
ethyl N-[3-(4-N,N-dimethylaminocarbonyl-5-methylacridin-9-yl)amino-5-hydroxymethyl]phenylcarbamate;
n-propyl N-[3-(4-N,N-dimethylaminocarbonyl-5-methyl-acridin-9-yl)amino-5-hydroxymethyl]phenylcarbamate
i-propyl N-[3-(4-N,N-dimethylaminocarbonyl-5-methyl-acridin-9-yl)amino-5-hydroxymethyl]phenylcarbamate;
n-butyl N-[3-(4-N,N-dimethylaminocarbonyl-5-methyl-acridin-9-yl)amino-5-hydroxymethyl]phenylcarbamate;
i-butyl N-[3-(4-N,N-dimethylaminocarbonyl-5-methyl-acridin-9-yl)amino-5-hydroxymethyl]phenylcarbamate;
t-butyl N-[3-(4-N,N-dimethylaminocarbonyl-5-methyl-acridin-9-yl)amino-5-hydroxymethyl]phenylcarbamate;
phenyl N-[3-(4-N,N-dimethylaminocarbonyl-5-methyl-acridin-9-yl)amino-5-hydroxymethyl]phenylcarbamate;
methyl N-[3-(4-aminocarbonyl-5-methoxyacridin-9-yl)-amino-5-hydroxymethyl]phenylcarbamate;
ethyl N-[3-(4-aminocarbonyl-5-methoxyacridin-9-yl)amino-5-hydroxymethyl]phenylcarbamate;
n-propyl N-[3-(4-aminocarbonyl-5-methoxyacridin-9-yl)-amino-5-hydroxymethyl]phenylcarbamate;
i-propyl N-[3-(4-aminocarbonyl-5-methoxyacridin-9-yl)-amino-5-hydroxymethyl]phenylcarbamate;
n-butyl N-[3-(4-aminocarbonyl-5-methoxyacridin-9-yl)-amino-5-hydroxymethyl]phenylcarbamate;
i-butyl N-[3-(4-aminocarbonyl-5-methoxyacridin-9-yl)-amino-5-hydroxymethyl]phenylcarbamate;
t-butyl N-[3-(4-aminocarbonyl-5-methoxyacridin-9-yl)-amino-5-hydroxymethyl]phenylcarbamate;
phenyl N-[3-(4-aminocarbonyl-5-methoxyacridin-9-yl)-amino-5-hydroxymethyl]phenylcarbamate;
methyl N-[3-(4-methylaminocarbonyl-5-methoxyacridin-9-yl)amino-5-hydroxymethyl]phenylcarbamate;
ethyl N-[3-(4-methylaminocarbonyl-5-methoxyacridin-9-yl)amino-5-hydroxymethyl]phenylcarbamate;
n-propyl N-[3-(4-methylaminocarbonyl-5-methoxyacridin-9-yl)amino-5-hydroxymethyl]phenylcarbamate;
i-propyl N-[3-(4-methylaminocarbonyl-5-methoxyacridin-9-yl)amino-5-hydroxymethyl]phenylcarbamate;
n-butyl N-[3-(4-methylaminocarbonyl-5-methoxyacridin-9-yl)amino-5-hydroxymethyl]phenylcarbamate;
i-butyl N-[3-(4-methylaiminocarbonyl-5-methoxyacridin-9-yl)amino-5-hydroxymethyl]phenylcarbamate;
t-butyl N-[3-(4-methylaminocarbonyl-5-methoxyacridin-9-yl)amino-5-hydroxymethyl]phenylcarbamate;
phenyl N-[3-(4-methylaminocarbonyl-5-methoxyacridin-9-yl)amino-5-hydroxymethyl]phenylcarbamate;
methyl N-[3-(4-N,N-dimethylaminocarbonyl-5-methoxy-acridin-9-yl)amino-5-hydroxymethyl]phenylcarbamate;
ethyl N-[3-(4-N,N-dimethylaminocarbanyl-5-methoxy-acridin-9-yl)amino-5-hydroxymethyl]phenylcarbamate;
n-propyl N-[3-(4-N,N-dimethylaminocarbonyl-5-methoxy-acridin-9-yl)amino-5-hydroxymethyl]phenylcarbamate;
i-propyl N-[3-(4-N,N-dimethylaminocarbonyl-5-methoxy-acridin-9-yl)amino-5-hydroxymethyl]phenylcarbamate;
n-butyl N-[3-(4-N,N-dimethylaminocarbonyl-5-methoxy-acridin-9-yl)amino-5-hydroxymethyl]phenylcarbamate;
i-butyl N-[3-(4-N,N-dimethylaminocarbonyl-5-methoxy-acridin-9-yl)amino-5-hydroxymethyl]phenylcarbamate;
t-butyl N-[3-(4-N,N-dimethylaminocarbonyl-5-methoxy-acridin-9-yl)amino-5-hydroxymethyl]phenylcarbamate;
phenyl N-[3-(4-N,N-dimethylaminocarbonyl-5-methoxy-acridin-9-yl)amino-5-hydroxymethyl]phenylcarbamate;
methyl N-[3-(acridin-9-yl)amino-5-acetyloxymethyl]-phenylcarbamate;
ethyl N-[3-(acridin-9-yl)amino-5-acetyloxymethyl]-phenylcarbamate;
n-propyl N-[3-(acridin-9-yl)amino-5-acetyloxymethyl]-phenylcarbamate;
i-propyl N-[3-(acridin-9-yl)amino-5-acetyloxymethyl]-phenylcarbamate;
n-butyl N-[3-(acridin-9-yl)amino-5-acetyloxymethyl]-phenylcarbamate;
i-butyl N-[3-(acridin-9-yl)amino-5-acetyloxymethyl]-phenylcarbamate;
t-butyl N-[3-(acridin-9-yl)amino-5-acetyloxymethyl]-phenylcarbamate;
phenyl N-[3-(acridin-9-yl)amino-5-acetyloxymethyl]-phenylcarbamate;
methyl N-[3-(acridin-9-yl)amino-5-acetyloxymethyl]-phenylcarbamate;
ethyl N-[3-(acridin-9-yl)amino-5-acetyloxymethyl]-phenylcarbamate;
methyl N-[3-(4-methylaminocarbonylacridin-9-yl)amino-5-acetyloxymethyl]phenylcarbamate;
ethyl N-[3-(4-methylaminocarbonylacridin-9-yl)amino-5-acetyloxymethyl]phenylcarbamate;
methyl N-[3-(4-methylaminocarbony-5-methylacridin-9-yl)-amino-5-acetyloxymethyl]phenylcarbamate;
ethyl N-[3-(4-methylaminocarbony-5-methylacridin-9-yl)-amino-5-acetyloxymethyl]phenylcarbamate;
methyl N-[3-(4-methylaminocarbony-5-methoxyacridin-9-yl)-amino-5-acetyloxymethyl]phenylcarbamate;
ethyl N-[3-(4-methylaminocarbony-5-methoxyacridin-9-yl)-amino-5-acetyloxymethyl]phenylcarbamate;
methyl N-[3-(4-methylaminocarbonyl-6-nitroacridin-9-yl)-amino-5-hydroxymethyl]phenylcarbamate;
ethyl N-[3-(4-methylaminocarbonyl-6-nitroacridin-9-yl)-amino-5-hydroxymethyl]phenylcarbamate;
methyl N-[3-(4-methylaminocarbonyl-7-nitroacridin-9-yl)-amino-5-hydroxymethyl]phenylcarbamate;
ethyl N-[3-(4-methylaminocarbonyl-7-nitroacridin-9-yl)-amino-5-hydroxymethyl]phenylcarbamate;
methyl N-[3-(4-methylaminocarbonyl-6-methylaminoacridin-9-yl)amino-5-hydroxymethyl]phenylcarbamate;
ethyl N-[3-(4-methylaminocarbonyl-6-methylaminoacridin-9-yl)amino-5-hydroxymethyl]phenylcarbamate;

methyl N-[3-(4-methylaminocarbonyl-7-methylaminoacridin-9-yl)amino-5-hydroxymethyl]phenylcarbamate;
ethyl N-[3-(4-methylaminocarbonyl-7-methylaminoacridin-9-yl)amino-5-hydroxymethyl]phenylcarbamate;
methyl N-[3-(3,6-dinitroacridin-9-yl)amino-5-hydroxymethyl]phenylcarbamate;
ethyl N-[3-(3,6-dinitroacridin-9-yl)amino-5-hydroxymethyl]phenylcarbamate;
methyl N-[3-(4,5-dinitroacridin-9-yl)amino-5-hydroxymethyl]phenylcarbamate;
ethyl N-[3-(4,5-dinitroacridin-9-yl)amino-5-hydroxymethyl]phenylcarbamate;
methyl N-{3-[3,6-bis(dimethylaminoethylamino)acridin-9-yl]amino-5-hydroxymethyl}phenylcarbamate;
ethyl N-{3-[3,6-bis(dimethylaminoethylamino)acridin-9-yl]amino-5-hydroxymethyl}phenylcarbamate;
methyl N-{3-[4,5-bis(dimethylaminoethylamino)acridin-9-yl]amino-5-hydroxymethyl}phenylcarbamate; and
ethyl N-{3-[4,5-bis(dimethylaminoethylamino)acridin-9-yl]amino-5-hydroxymethyl}phenylcarbamate.

3. The compound of claim 2 selected from the group consisting of:
methyl N-[3-(acridin-9-yl)amino-5-hydroxymethyl]phenylcarbamate;
ethyl N-[3-(acridin-9-yl)amino-5-hydroxymethyl]phenylcarbamate;
n-propyl N-3-[(acridin-9-yl)amino-5-hydroxymethyl]phenyl-carbamate;
phenyl N-[3-(acridin-9-yl)amino-5-hydroxymethyl]phenylcarbamate;
ethyl N-[3-(4-methylacridin-9-yl)amino-5-hydroxymethyl]phenylcarbamate;
ethyl N-[3-(4-nitroacridin-9-yl)amino-5-hydroxymethyl]phenylcarbamate;
ethyl N-[3-(4-hydroxycarbonylacridin-9-yl)amino-5-hydroxymethyl]phenylcarbamate;
ethyl N-[3-(4-methoxycarbonylacridin-9-yl)amino-5-hydroxymethyl]phenylcarbarate;
ethyl N-[3-(4-aminocarbonylacridin-9-yl)amino-5-hydroxymethyl]phenylcarbamate;
ethyl N-[3-(4-methylaminocarbonylacridin-9-yl)amino-5-hydroxymethyl]phenylcarbamate;
ethyl N-[3-(4-N,N-dimethylaminacarbonylacridin-9-yl)amino-5-hydroxymethyl]phenylcarbanate;
ethyl N-[3-(4-methoxyacridin-9-yl)amino-5-hydroxymethyl]-phenylcarbamate;
ethyl N-[3-(3-chloroacridin-9-yl)amino-5-hydroxymethyl]phenylcarbamate;
ethyl N-[3-(4-chloroacridin-9-yl)amino-5-hydroxymethyl]phenylcarbamate;
ethyl N-[3-(4-methylaminocarbonyl-5-methylacridin-9-yl)-amino-5-hydroxymethyl]phenylcarbamate;
ethyl N-[3-(4-N,N-dimethylaminocarbonyl-5-methylacridin-9-yl)amino-5-hydroxymethyl]phenylcarbamate;
ethyl N-[3-(4-chloroacridin-9-yl)amino-5-hydroxymethyl]phenycarbamate;
ethyl N[3-(4-methylaminocarbonyl-5-methoxyacridin-9-yl)-amino-5-hydroxymethyl]phenylcarbamate;
ethyl N-[3-(4-N,N-dimethylaminocarbonyl-5-methoxyacridin-9-yl)amino-5-hydroxymethyl]phenylcarbamate; and
ethyl N-[3-(3-methylaminocarbonyl-5-nitroacridin-9-yl)-amino-5-hydroxymethyl]phenylcarbamate.

4. The compound of claim 3 which is ethyl N-[3-(acridin-9-yl)amino-5-hydroxymethyl]phenylcarbamate.

5. A pharmaceutical composition which comprises as the active ingredient an effective amount of the compound of Formula (I)

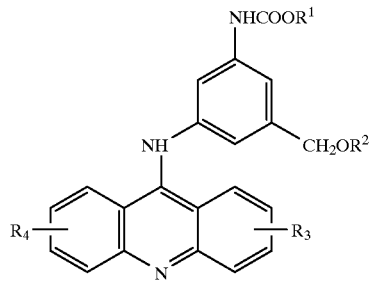

wherein $R^1$ is $C_{1-6}$ alkyl; or phenyl;

$R^2$ is hydrogen;
an acyl group of the formula —$COR^a$ wherein $R^a$ is $C_{1-6}$ alkyl or phenyl; or
an acetylalkylcarbonyl group of the formula —CO$(CH_2)_n COCH_3$ wherein n=1–3; and $R^3$ and $R^4$ are substituents at different positions of the acridine ring (i.e. C-1'–C-8'), and $R^3$ and $R^4$ may be the same or different and independently represent:
hydrogen;
$C_{1-6}$ alkyl;
$C_{1-6}$ alkyloxy;
a nitro group;
an aminoalkylamino group of the formula —$NH(CH_2)_n NR^d R^e$ wherein $R^d$ and $R^e$ may be the same or different and independently represent hydrogen, $C_{1-6}$ alkyl, a hydroxyalkyl group of the formula —$(CH_2)_n OH$ wherein n=1–3, or $C_{1-6}$ haloalkyl;
an alkylaminocarbonyl group of the formula —$CONHR^f$ wherein $R^f$ is $C_{1-6}$ alkyl;
an alkylaminoalkylaminocarbonyl group of the formula —$CONH(CH_2)_n NR^g R^h$ wherein n=1–5, and $R^g$ and $R^h$ may be the same or different and independently represent hydrogen, or $C_{1-6}$ alkyl;
a halogen group;
a carbamate group of the formula —$CH_2 CONHR^f$ wherein $R^f$ is as defined above;
an alkylcarbonyloxymethyl group of the formula —$CH_2 OCOR^f$ wherein $R^f$ is as defined above;
an alkyl sulfonate of the formula —$SO_3 R^f$ wherein $R^f$ is as defined above; and
an alkylsulfonyl group of the formula —$SO_2 R^f$ wherein $R^f$ is as defined above;

and the pharmaceutically acceptable salts thereof;

in combination with a pharmaceutically acceptable carrier thereof.

6. A method for inhibiting growth of tumor cells which comprises contacting the tumor cells with an effective amount of the compound of Formula (I)

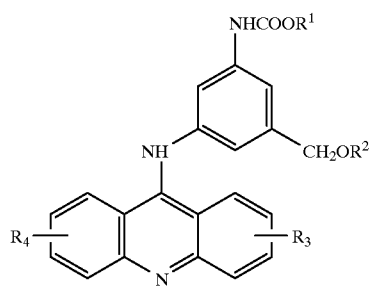

Formula (I)

wherein
$R^1$ is $C_{1-6}$ alkyl; or phenyl;
$R^2$ is hydrogen;
 an acyl group of the formula —$COR^a$ wherein $R^a$ is $C_{1-6}$ alkyl or phenyl; or
 an acetylalkylcarbonyl group of the formula —CO$(CH_2)_n COCH_3$ wherein n=1–3; and
$R^3$ and $R^4$ are substituents at different positions of the acridine ring (i.e. C-1'–C-8'), and $R^3$ and $R^4$ may be the same or different and independently represent:
hydrogen;
$C_{1-6}$ alkyl;
$C_{1-6}$ alkyloxy;
a nitro group;
an aminoalkylamino group of the formula —$NH(CH_2)_n NR^d R^e$ wherein $R^d$ and $R^e$ may be the same or different and independently represent hydrogen, $C_{1-6}$ alkyl, a hydroxyalkyl group of the formula —$(CH_2)_n OH$ wherein n=1–3, or $C_{1-6}$ haloalkyl;
an alkylaminocarbonyl group of the formula —$CONHR^f$ wherein $R^f$ is $C_{1-6}$ alkyl;
an alkylaminoalkylaminocarbonyl group of the formula —$CONH(CH_2)_n NR^g R^h$ wherein n=1–5, and $R^g$ and $R^h$ may be the same or different and independently represent hydrogen, or $C_{1-6}$ alkyl;
a halogen group;
a carbamate group of the formula —$CH_2 CONHR^f$ wherein $R^f$ is as defined above;
an alkylcarbonyloxymethyl group of the formula —$CH_2 OCOR^f$ wherein $R^f$ is as defined above;
an alkyl sulfonate of the formula —$SO_3 R^f$ wherein $R^f$ is as defined above; and
an alkylsulfonyl group of the formula —$SO_2 R^f$ wherein $R^f$ is as defined above;
and the pharmaceutically acceptable salts thereof.

* * * * *